United States Patent
Purchase, Jr. et al.

(10) Patent No.: US 6,399,612 B1
(45) Date of Patent: Jun. 4, 2002

(54) HETEROARYL BUTYRIC ACIDS AND THEIR DERIVATIVES AS INHIBITORS OF MATRIX METALLOPROTEINASES

(75) Inventors: Claude Forsey Purchase, Jr., Ann Arbor; Bruce David Roth, Plymouth; Gerald Paul Schielke; Lary Craswell Walker, both of Ann Arbor; Andrew David White, Pinckney, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/647,400

(22) PCT Filed: Sep. 23, 1998

(86) PCT No.: PCT/US98/19875

§ 371 Date: Oct. 23, 2000

(87) PCT Pub. No.: WO99/18079

PCT Pub. Date: Apr. 15, 1999

Related U.S. Application Data

(60) Provisional application No. 60/061,012, filed on Oct. 6, 1997.

(51) Int. Cl.$^7$ .................... A61K 31/495; A61K 31/415; A61K 31/381; A61K 31/34; C07D 333/28
(52) U.S. Cl. .................. 514/252.01; 514/396; 514/403; 514/438; 514/461; 514/549; 514/29; 514/72; 514/73; 514/229
(58) Field of Search ............................ 514/252.01, 396, 514/403, 438, 461; 549/29, 72, 73, 229

(56) References Cited

FOREIGN PATENT DOCUMENTS

| WO | WO 96/15096 | 11/1995 |
| WO | WO 96/38434 | 4/1996 |
| WO | WO 96/15096 | * 5/1996 |
| WO | WO 98/09940 | 8/1997 |

OTHER PUBLICATIONS

Child R.G. et al."A new Nonsteroidal antiinf. . . ",Arzn.–Forsch. 30/4A,695–702, (1980).*
"The Canadian Study of Health and Aging: Risk Factors for Alzheimer's Disease in Canada," Neurology 44, Nov. 1994, pp. 2073–2080.
P.S. Aisen, "Anti–inflammatory Therapy for Alzheimer's Disease," Neurobiology of Aging 21 (2000) 447–448.
K. Anderson et al., "Do Nonsteroidal Anti–inflammatory Drugs Decrease the Risk for Alzheimer's Disease? The Rotterdam Study," Neurology 45, Aug. 1995, pp. 1441–1445.
H. J. Andrews et al., "A Synthetic Peptide Metalloproteinase Inhibitor, but not Timp, Prevents the Breakdown of Proteoglycan Whitin Articular Cartilage in vitro," Agents Actions 37 (1992), pp. 147–154.
P.W. Armstrong et al., "Structural Remodelling in Heart Failure: Gelatinase Induction," Can J. Cardiol. vol. 10, No. 2, Mar. 1994, pp. 214–220.
R. Benelli et al., "Inhibition of ADIS–Kapori's Sarcoma Cell Induced Endothelial Cell Invasion by TIMP–2 and a Synthetic Peptide from the Metalloproteinase Propeptide: Implications for an Anti–Angiogenic Therapy," Oncology Research, vol. 6, pp. 251–257, 1994.
J.C.S. Breitner et al., "Delayed Onset of Alzheimer's Disease With Nonsteroidal Anti–Inflammatory and Histamine H2 Blocking Drugs," Neurobiology of Aging, vol. 16, No. 4, pp. 523–530, 1995.
J.C.S. Breitner et al., "Inverse Association of Anti–Inflammatory Treatments and Alzheimer's Disease: Intitial Results of a Co–Twin Control Study," Neurology, 44, Feb. 1994, pp. 227–232.
S.J. Brown et al., "Collagenolytic Activity of Alkali–Burned Corneas," Arch. Ophthal. vol. 81, Mar. 1969, pp. 370–373.
F.R. Burns, "Inhibition of Purified Collagenase from Alkali–Burned Rabbit Corneas," Investigative Opthalmology & Visual Science, vol. 30, No. 7, Jul. 1989, pp. 1569–1575.
M.P. Bendeck et al., "Smooth Muscle Cell Migration and Matrix Metalloproteinase Expression After Arterial Injury in the Rat," Circulation Research, vol. 75, No. 3, Sep. 1994, pp. 539–545.
R.G. Child, "Fenbufen, a New Anti–Inflammatory Analgesic: Synthesis and Structure–Activity Relationships of Analogs," Journal of Pharmaceutical Sciences, vol. 66, No. 4, Apr. 1977, pp. 466–476.
U. Lucca et al., "Nonsteroidal Antiinflammatory Drug Use in Alzheimer's Disease," Biol. Psychiatry, 1994; 36:854–856.
T.I. Mandybur et al., "Cerebral Amyloid Angiopathy With Granulomatous Angiitis Ameliorated by Steroid–Cytoxan Treatment," Clinical Neuropharmacology, vol. 15, No. 3, pp. 241–247.

(List continued on next page.)

Primary Examiner—Mukund J. Shah
Assistant Examiner—Sudhaker B. Patel
(74) Attorney, Agent, or Firm—Merchant & Gould P.C.

(57) ABSTRACT

Heteroaryl butyric acid compounds and derivatives are described as well as methods for the preparation and pharmaceutical compositions of same, which are useful as inhibitors of matrix metalloproteinases, particularly gelatinase A, collagenase-3, and stromelysin-1 and for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, osteoporosis, or other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

47 Claims, No Drawings

OTHER PUBLICATIONS

R. Martin et al., "Immunological Aspects of Demyelinating Diseases," Annu. Rev. Immunol. 1992, 10:153–87.

R. Martin et al., "Immunological Aspects of Experimental Allergic Encephalomyelitis and Multiple Sclerosis," Critical Reviews in Clinical Laboratory Sciences, 32(2):121–182 (1995).

E.G. McGeer et al., "Neurodegeneration and the Immune System," In: Calne D.B., ed. Neurodegenerative Diseases, W. B. Saunders, 1994:277–300.

P.L.McGeer et al., "Anti–inflammatory Agents as a Therapeutic Approach to Alzheimer's Disease," Neurology 42, Feb. 1992, pp. 447–449.

P.L. McGeer et al., "Neuroimmune Mechanisms in Alzheimer Disease Pathogenesis," Alzheimer Disease and Associated Disorders, vol. 8, No. 3, pp. 149–158.

A. Melchiori et al., "Inhibition of Tumor Cell Invasion by a Highly Conserved Peptide Sequence from the Matrix Metalloproteinase Enzyme Prosegment," Cancer Research 52, 2353–2356, Apr. 15, 1992.

W.L. Monsky et al., "Binding and Localization of $M_r$ 72,000 Matrix Metalloproteinase at Cell Surface Invadopodia," Cancer Research 53, 2159–3164, 1993.

C.M. Overall et al., "Demonstration of Tissue Collagenase Activity in vivo and its Relationship to Inflammation Severity in Human Gingiva," Journal of Periodontal Research; 1987: 22: 81–88.

P.H. Patterson, "Cytokines in Alzheimer's Disease and Multiple Sclerosis," Current Opinion in Neurobiology 1995, 5:642–646.

R.R. Pauly et al., "Migration of Cultured Vascular Smooth Muscle Cells Through a Basement Membrane Barrier Requires Type IV Collagenase Activity and is Inhibited by Cellular Differentiation," Circulation Research, vol. 75, No. 1, Jul. 1994, pp. 41–54.

H.K. Reddy et al., "Activated Myocardial Collagenase in Idiopathic Dilated Cardiomyopathy: A Marker of Dilatation and Remodeling," Clinical Research, vol. 41, No. 3, 1993, 660A Only Abstract.

J.B. Rich et al., "Nonsteroidal Antiinflammatory Drugs in Alzheimer's Disease," Neurology 45, Jan. 1995, pp. 51–55.

J. Rogers et al., "Inflammation and Alzheimer's Disease Pathogenesis," Neurobiology of Aging, vol. 17, No. 5, pp. 681–686, 1996.

A.M. Romanic et al., "The Induction of 72–kD Gelatinase in T Cells Upon Adhesion to Endothelial Cells is VCAM–1 Dependent," The Journal of Cell Biology, vol. 125, No. 5, Jun. 1994, 1165–1178.

N.J. Rothwell et al., "Involvement of Cytokines in Acute Neurodegeneration in the CNS," Neuroscience and Biobehavioral Reviews, vol. 17, pp. 217–227, 1993.

U.K. Saarialho–Kere et al., "Distinct Populations of Basal Keratinocytes Express Stomelysin–1 and Stromelysin–2 in Chronic Wounds," J. Clin. Invest., vol. 94, Jul. 1994, 79–88.

H.N. Sabbah et al., "Left Ventricular Shape Changes During the Course of Evolving Heart Failure," Am. J. Physiol., 1992;263:H266–270.

H. Sato et al., "A Matrix Metalloproteinase Expressed on the Surface of Invasive Tumour Cells," Nature, vol. 370, Jul. 7, 1994, 61–65.

A.Y. Strongin, et al., "Plasma Membrane–Dependent Activation of the 72–kDa Type IV Collagenase Is Prevented by Complex Formation with TIMP–2," The Journal of Biological Chemistry, vol. 268, No. 19, Jul. 5, 1993, 14033–14039.

G. Taraboletti et al., "Inhibition of Angiogenesis and Murine Hemangioma Growth by Batimastat, a Synthetic Inhibitor of Matrix Metalloproteinase," Journal of the National Cancer Institute, vol. 87, No. 4, Feb. 15, 1995, 293–298.

S.C. Tyagi et al., Myocardial Collagenase in Falling Human Heart, Clinical Research, vol. 41, No. 3, 1993, 681A Abstract.

V. Uitto et al., "Collagenase and Neutral Metallo–Proteinase Activity in Extracts of Inflamed Human Gingiva," Journal of Periodontal Research 16: 417–424, 1981.

N. Vine et al., "Metalloproteinase in Degenerative Aortic Disease," Clinical Science (1991) 81, 223–239.

L.A. Walakovits et al., "Detection of Stomelysin and Collagenase in Synovial Fluid from Patients with Rheumatoid Arthritis and Posttraumatic Knee Injury," Arthritis and Rheumatism, vol. 35, No. 1, Jan. 1992, 35–42.

J.F. Woessner, Jr., "Matrix Metalloproteinases and Their Inhibitors in Conective Tissue Remodling," The FASEB Journal, vol. 5, May 1991, 2145–2154.

M. Zafarullah et al., "Elevated Metalloproteinase and Tissue Inhibitor of Metalloproteinase mRNA in Human Osteoarthritic Synovia," The Journal of Rheumatology 1993; 20:P4, 693–697.

"The Canadian Study of Health and Aging: Risk Factors for Alzheimer's Disease in Canada," Neurology 44, Nov. 1994, pp. 2073–2080.

P.S. Aisen, "Anti–inflammatory Therapy for Alzheimer's Disease," Neurobiology of Aging 21 (2000) 447–448.

K. Anderson et al., "Do Nonsteroidal Anti–inflammatory Drugs Decrease the Risk for Alzheimer's Disease? The Rotterdam Study," Neurology 45, Aug. 1995, pp. 1441–1445.

H. J. Andrews et al., "A Synthetic Peptide Metalloproteinase Inhibitor, but not Timp, Prevents the Breakdown of Proteoglycan Within Articular Cartilage in vitro," Agents Actions 37 (1992), pp. 147–154.

P.W. Armstrong et al., "Structural Remodelling in Heart Failure: Gelatinase Induction," Can J. Cardiol. vol. 10, No. 2, Mar. 1994, pp. 214–220.

R. Benelli et al., "Inhibition of ADIS–Kaposi's Sarcoma Cell Induced Endothelial Cell Invasion by TIMP–2 and a Synthetic Peptide from the Metalloproteinase Propeptide: Implications for Anti–Angiogenic Therapy," Oncology Research, vol. 6, No. 6, pp. 251–257, 1994.

J.C.S. Breitner et al., "Delayed Onset of Alzheimer's Disease With Nonsteroidal Anti–Inflammatory and Histamine H2 Blocking Drugs," Neurobiology of Aging, vol. 16, No. 4, pp. 523–530, 1995.

J.C.S. Breitner et al., "Inverse Association of Anti–Inflammatory Treatments and Alzheimer's Disease: Initial Results of a Co–Twin Control Study," Neurobiology, 44, Feb. 1994, pp. 227–232.

S.J. Brown et al., "Collagenolytic Activity of Alkali–Burned Corneas," Arch. Ophthal. vol. 81, Mar. 1969, pp. 370–373.

F.R. Burns, "Inhibition of Purified Collagenase from Alkali–Burned Rabbit Corneas," Investigative Ophthalmology & Visual Science, vol. 30, No. 7, Jul. 1989, pp. 1569–1575.

M.P. Bendeck et al., "Smooth Muscle Cell Migration and Matrix Metalloproteinase Expression After Arterial Injury in the Rat," Circulation Research, vol. 75, No. 3, Sep. 1994, pp. 539–545.

R.G. Child, "Fenbufen, a New Anti–Inflammatory Analgesic: Synthesis and Structure–Activity Relationships of Analogs," Journal of Pharmaceutical Sciences, vol. 66, No. 4, Apr. 1977, pp. 466–476.

U. Lucca et al., "Nonsteroidal Antiinflammatory Drug Use in Alzheimer's Disease," Biol. Psychiatry, 1994; 36:854–856.

T.I. Mandybur et al., "Cerebral Amyloid Angiopathy With Granulomatous Angiitis Ameliorated by Steroid–Cytoxan Treatment," Clinical Neuropharmacology, vol. 15, No. 3, pp. 241–247.

R. Martin et al., "Immunological Aspects of Demyelinating Diseases," Annu. Rev. Immunol. 1992, 10:153–87.

R. Martin et al., "Immunological Aspects of Experimental Allergic Encephalomyelitis and Multiple Sclerosis," Critical Reviews in Clinical Laboratory Sciences, 32(2):121–182 (1995).

E.G. McGeer et al., "Neurodegeneration and the Immune System," In: Calne D.B., ed. Neurodegenerative Diseases, W.B. Saunders, 1994:277–300.

P.L.McGeer et al., "Anti–inflammatory Agents as a Therapeutic Approach to Alzheimer's Disease," Neurology 42, Feb. 1992, pp. 447–449.

P.L. McGeer et al., "Neuroimmune Mechanisms in Alzheimer Disease Pathogenesis," Alzheimer Disease and Associated Disorders, vol. 8, No. 3, pp. 149–158.

A. Melchiori et al., "Inhibition of Tumor Cell Invasion by a Highly Conserved Peptide Sequence from the Matrix Metalloproteinase Enzyme Prosegment," Cancer Research 52, 2353–2356, Apr. 15, 1992.

W.L. Monsky et al., "Binding and Localization of $M_r$ 72,000 Matrix Metalloproteinase at Cell Surface Invadopodia," Cancer Research 53, 3159–3164, 1993.

C.M. Overall et al., "Demonstration of Tissue Collagenase Activity in vivo and its Relationship to Inflammation Severity in Human Gingiva," Journal of Periodontal Research; 1987: 22: 81–88.

P.H. Patterson, "Cytokines in Alzheimer's Disease and Mutliple Sclerosis," Current Opinion in Neurobiology 1995, 5:642–646.

R.R. Pauly et al., "Migration of Cultured Vascular Smooth Muscle Cells Through a Basement Membrane Barrier Requires Type IV Collagenase Activity and is Inhibited Cellular Differentiation," Circulation Research, vol. 75, No. 1, Jul. 1994, pp. 41–54.

H.K. Reddy et al., "Activated Myocardial Collagenase in Idiopathic Dilated Cardiomyopathy: A Marker of Dilatation and Remodeling," Clinical Research, vol. 41, No. 3, 1993, 660A Only Abstract.

J.B. Rich et al., "Nonsteroidal Antiinflammatory Drugs in Alzheimer's Disease," Neurology 45, Jan. 1995, pp. 51–55.

J. Rogers et al., "Inflammation and Alzheimer's Disease Pathogenesis," Neurobiology of Aging, vol. 17, No. 5, pp. 681–686, 1996.

A.M. Romanic et al., "The Induction of 72–kD Gelatinase in T Cells Upon Adhesion to Endothelial Cells is VCAM–1 Dependent," The Journal of Cell Biology, vol. 125, No. 5, Jun. 1994, 1165–1178.

N.J. Rothwell et al., "Involvement of Cytokines in Acute Neurodegeneration in the CNS," Neuroscience and Biobehavioral Reviews, vol. 17, pp. 217–227, 1993.

U.K. Saarialho–Kere et al., "Distinct Populations of Basal Keratinocytes Express Stromelysin–1 and Stromelysin–2 in Chronic Wounds," J. Clin. Invest., vol. 94, Jul. 1994, 79–88.

H.N. Sabbah et al., "Left Ventricular Shape Changes During the Course of Evolving Heart Failure," Am. J. Physiol., 1992;263:H266–270.

H. Sato et al., "A Matrix Metalloproteinase Expressed on the Surface of Invasive Tumour Cells," Nature, vol. 370, Jul. 7, 1994, 61–65.

A.Y. Strongin, et al., "Plasma Membrane–Dependent Activation of the 72–kDa Type IV Collagenase Is Prevented by Complex Formation with TIMP–2," The Journal of Biological Chemistry, vol. 268, No. 19, Jul. 5, 1993, 14033–14039.

G. Taraboletti et al., "Inhibition of Angiogenesis and Murine Hemangioma Growth by Batimastat, a Synthetic Inhibitor of Matrix Metalloproteinase," Journal of the National Cancer Institute, vol. 87, No. 4, Feb. 15, 1995, 293–298.

S.C. Tyagi et al., Myocardial Collagenase in Failing Human Heart, Clinical Research, vol. 41, No. 3, 1993, 681A Abstract.

V. Uitto et al., "Collagenase and Neutral Metallo–Proteinase Activity in Extracts of Inflamed Human Gingiva," Journal of Periodontal Research 16: 417–424, 1981.

N. Vine et al., "Metalloproteinase in Degenerative Aortic Disease," Clinical Science (1991) 81, 223–239.

L.A. Walakovits et al., "Detection of Stomelysin and Collagenase in Synovial Fluid from Patients with Rheumatoid Arthritis and Posttraumatic Knee Injury," Arthritis and Rheumatism, vol. 35, No. 1, Jan. 1992, 35–42.

J.F. Woessner, Jr., "Matrix Metalloproteinases and Their Inhibitors in Connective Tissue Remodelling," The FASEB Journal, vol. 5, May 1991, 2145–2154.

M. Zafarullah et al., "Elevated Metalloproteinase and Tissue Inhibitor of Metalloproteinase mRNA in Human Osteoarthritic Synovia," The Journal of Rheumatology 1993; 20:4, 693–697.

* cited by examiner

HETEROARYL BUTYRIC ACIDS AND THEIR DERIVATIVES AS INHIBITORS OF MATRIX METALLOPROTEINASES

This application claims priority from provisional application Ser. No. 60/061,012, filed Oct. 6, 1997.

BACKGROUND OF THE INVENTION

The present invention relates to novel heteroaryl butyric acid compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (MMP-2), collagenase-3 (MMP-13), and stromelysin-1 (MMP-3). More particularly, the novel compounds of the present invention are useful in the treatment of atherosclerotic plaque rupture, aortic aneurism, heart failure, restenosis, periodontal disease, corneal ulceration, treatment of burns, decubital ulcers, wound repair, cancer, inflammation, pain, arthritis, osteoporosis, multiple sclerosis, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MMP) family (Woessner J. F., *FASEB J.*, 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C., *J. Biol. Chem.*, 1994;269:16766–16773), and the newly discovered membrane-associated matrix metalloproteinases (Sato H., Takino T., Okada Y., Cao I., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxymates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.*, 1991;81:233–239).

Heart failure arises from a number of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy", *Clin. Res.*, 1993;41:660A; Tyagi S. C., Reddy H. K., Voelker D., Tjara I. E., and Weber K. T., "Myocardial collagenase in failing human heart", *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction", *Can. J. Cardiol.*, 1994; 10:214–220), and cardiac dilation precedes profound deficits in cardiac function (Sabbah H. N., Kono T., Stein P. D., Mancini G. B., and Goldstein S., "Left ventricular shape changes during the course of evolving heart failure", *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat", *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation", *Circulation Research*, 1994;75:41–54).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva", *J. Periodontal Res.*, 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva", *J. Periodontal Res.*, 1987;22:81–88). Proteolytic degradation of extracellular matrix has been observed in corneal ulceration following alkali burns (Brown S. I., Weller C. A., and Wasserman H. E., "Collagenolytic activity of alkali burned corneas", *Arch. Ophthalmol.*, 1969;81:370–373). Thiol-containing peptides inhibit the collagenase isolated from alkali-burned rabbit corneas (Burns F. R., Stack M. S., Gray R. D., and Paterson C. A., *Invest. Ophthalmol.*, 1989;30:1569–1575).

Stromelysin is produced by basal keratinocytes in a variety of chronic ulcers (Saarialho-Kere U. K., Ulpu K., Pentland A. P., Birkedal-Hansen H., Parks W. O., and Welgus H. G., "Distinct Populations of Basal Keratinocytes Express Stromelysin-1 and Stromelysin-2 in Chronic Wounds", *J. Clin. Invest.*, 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies, et al., (*Cancer Res.*, 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356). The natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Marmer B. L., Grant G. A., and Goldberg G. I., *J. Biol. Chem.*, 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., *Cancer Res.*, 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute*, 1995;87:293 and Benelli R., Adatia R., Ensoli B., Stetler-Stevenson W. G., Santi L., and Albini A, *Oncology Research*, 1994;6:251–257).

Several investigators have demonstrated consistent elevation of stromelysin and collagenase in synovial fluids from osteo- and rheumatoid arthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", *Arthritis Rheum.*, 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", *J. Rheumatol.*, 1993;20:693–697). TIMP-1 and TIMP-2 prevented the formation of collagen fragments, but not proteoglycan fragments in both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Biophys. Res. Commun.*, 1994;201:94–101).

Gijbels, et al., (*J. Clin. Invest.*, 1994;94:2177–2182) recently described a peptide hydroxamate, GM6001, that suppressed the development or reversed the clinical expression of experimental autoimmune encephalomyelitis (EAE) in a dose dependent manner, suggesting the use of MMP inhibitors in the treatment of autoimmnune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent", *J. Cell Biology*, 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G., and McGeer P. L., "Neurodegeneration and the immune system", In: Calne D. B., ed. Neurodegenerative Diseases, W. B. Saunders, 1994:277–300). Other disorders that may involve neuroinflanmmatory mechanisms include amyotrophic lateral sclerosis (Leigh P. N., "Pathogenic mechanisms in amyotrophic lateral sclerosis and other motor neuron disorders", In: Calne D. B., ed., Neurodegenerative Diseases, W. B. Saunders, 1994:473–88), cerebral amyloid angiopathy (Mandybur T. I. and Balko G., "Cerebral amyloid angiopathy with granulomatous angiitis ameliorated by steroid-cytoxan treatment", *Clin. Neuropharm.*, 1992;15:241–7), AIDS (Gendelman H. E. and Tardieu M., "Macrophages/microglia and the pathophysiology of CNS injuries in AIDS", *J. Leukocyte Biol.*, 1994;56:387–8), Parkinson's disease, Huntington's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases", *Annul Rev. Immunol.*, 1992;10:153–87; Clark R. K., Lee E. V., Fish C. J., et al., "Development of tissue damage, inflammation and resolution following stroke: an immunohistochemical and quantitative planimetric study", *Brain Res. Bull.*, 1993;31:565–72;

Giulian D. and Vaca K., "Inflammatory glia mediate delayed neuronal damage after ischemia in the central nervous system", *Stroke*, 1993;24(Suppl 12):184–90; Patterson P. H., "Cytokines in Alzheimer's disease and multiple sclerosis", *Cur. Opinion Neurobiol.* 1995;5:642–6; McGeer P. L., Rogers J., and McGeer E. G., "Neuroimmune mechanisms in Alzheimer disease pathogenesis", *Alzheimer Dis. Assoc. Disorders*, 1994;8:149–58; Martin R. and McFarland H. F., "Immunological aspects of experimental allergic encephalomyelitis and multiple sclerosis", *Crit. Rev. Clin. Lab. Sci.*, 1995;32:121–82; Rogers J., Webster S., Lue L. F., et al., "Inflammation and Alzheimer's disease pathogenesis", In: *Neurobiology of Aging*, 1996;17:681–686; Rothwell N. J. and Relton J. K., "Involvement of cytokines in acute neurodegeneration in the CNS", *Neurosci. Biobehav. Rev.*, 1993;17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G. and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer, et al., supra., 1994; Rogers, et al., supra.); 2) There is evidence that β-amyloid induces neurodegenerative changes primarily through interactions with inflammatory molecules, and that inflammation alone is sufficient to induce neurodegeneration (Rogers et al., supra); and 3) Growing epidemiological data indicate that antiinflammatory therapy can delay the onset and slow the progression of Alzheimer's disease (McGeer P. L. and Rogers J., "Anti-inflammatory agents as a therapeutic approach to Alzheimer's disease", *Neurology*, 1992;42:447–9; Canadian Study of Health and Aging, "Risk factors for Alzheimer's disease in Canada", *Neurology*, 1994;44:2073–80; Lucca U., Tettarnanti M., Forloni G., and Spagnoli A., "Nonsteroidal antiinflammatory drug use in Alzheimer's disease", *Biol. Psychiatry*, 1994;36:854–66; Hampel H. and Müller N., "Inflammatory and immunological mechanisms in Alzheimer's disease", *DN&P*, 1995;8:599–608; Breitner J. C. S., Gau B. A., Welsh K. A., et al., "Inverse association of anti-inflammatory treatments and Alzheimer's disease: Initial results of a co-twin control study", *Neurology*, 1994;44:227–32; Breitner J. C. S., Welsh K. A., Helms M. J., et al., "Delayed onset of Alzheimer's disease with nonsteroidal anti-inflammatory and histamine H2 blocking drugs", *Neurobiol. Aging*, 1995;16:523–30; Andersen K., Launcr L. J., Ott A., Hoes A. W., Breteler M. M. B., and Hofman A., "Do nonsteroidal anti-inflammatory drugs decrease the risk for Alzheimer's disease? The Rotterdam Study", *Neurology*, 1995;45:1441–5; Rich J. B., Rasmusson D. X., Folstein M. F., et al., "Nonsteroidal anti-inflammatory drugs in Alzheimer's disease", *Neurology*, 1995;45:51–5; Aisen P. S., "Anti-inflammatory therapy for Alzheimer's disease", *Dementia*, 1995;9:173–82; Rogers, et al., supra). Chronic use of nonsteroidal antiinflammatory drugs (NSAIDs), most commonly for the treatment of rheumatoid arthritis, decreases the probability of developing Alzheimer's disease, and there is reason to believe that other antiinflammatory agents may also be effective, although direct evidence for the efficacy of such treatments is lacking (Hamper and Muller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as antiinflammatory/immuno-suppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An antiinflammatory drug that is well-tolerated by patients and that crosses the blood-brain barrier has significant advantages for the treatment of acute and chronic degenerative diseases of the central nervous system.

Copending U.S. patent applications Ser. No. 60/025,814, filed Sep. 4, 1996, and Ser. No. 60/027,138, filed Oct. 2, 1996, disclose a series of biphenyl butyric acids as inhibitors of matrix metalloproteinases.

We have identified a series of heteroaryl butyric acid compounds and their derivatives that are inhibitors of matrix metalloproteinases, particularly collagenase-3, stromelysin-1 and gelatinase A, and thus useful as agents for the treatment of multiple sclerosis, atherosclerotic plaque, rupture, restenosis, aortic aneurism, heart failure, periodontal disease, corneal ulceration, treatment of burns, decubital ulcers, wound repair, cancer, inflammation, pain, arthritis, osteoporosis, or other autoimmune or inflammatory diseases dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, a first aspect of the present invention is a compound of Formula I

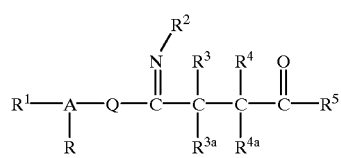

wherein A is

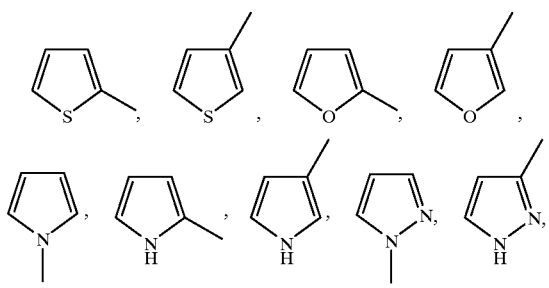

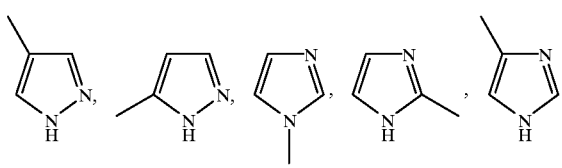
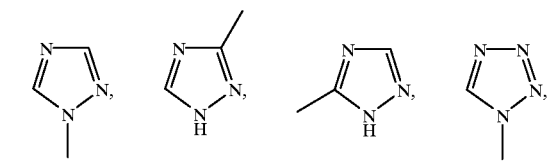
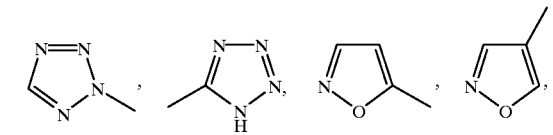
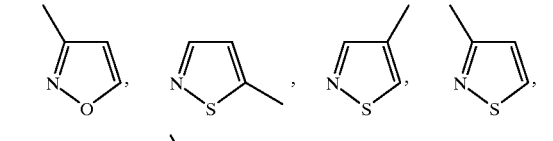
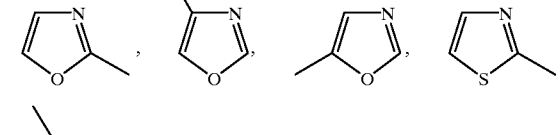
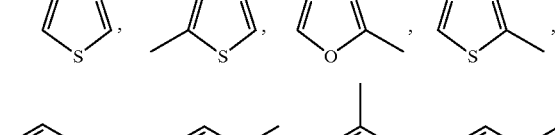
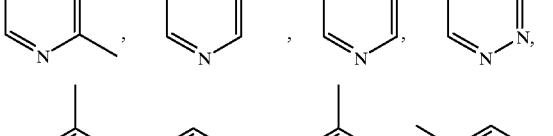
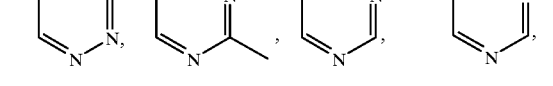
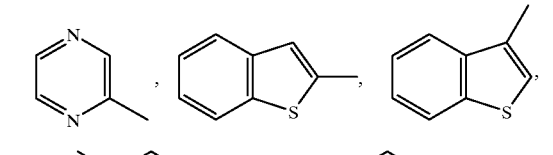
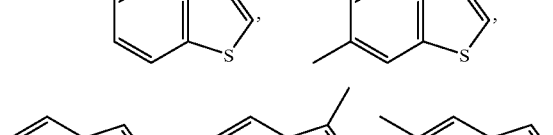
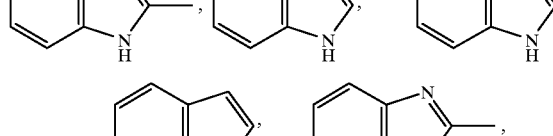

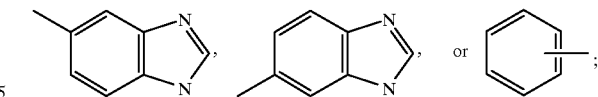

Q is 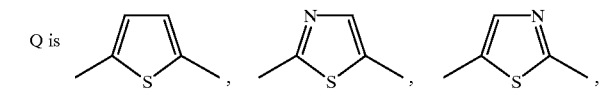

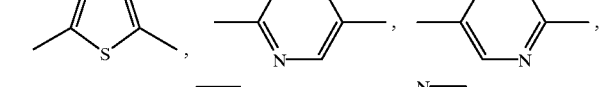

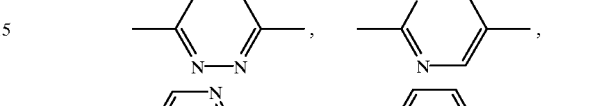

R and $R^1$ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
  alkyl,
  aryl,
  arylalkyl,
  heteroaryl, or
  cycloalkyl,

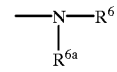

wherein $R^6$ and $R^{6a}$ are the same or different and are as defined above for $R^6$,

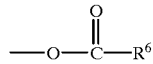

wherein $R^6$ is as defined above,

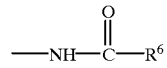

wherein $R^6$ is as defined above,

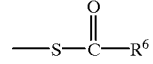

wherein $R^6$ is as defined above,

—SR⁶ wherein R⁶ is as defined above,

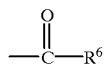

wherein R⁶ is as defined above,
—CH₂—OR⁶ wherein R⁶ is as defined above,

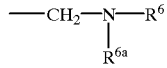

wherein R⁶ and R⁶ᵃ are the same or different and are as defined above for R⁶,

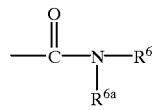

wherein R⁶ and R⁶ᵃ are the same or different and are as defined above for R⁶,

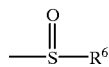

wherein R⁶ is as defined above,

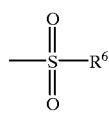

wherein R⁶ is as defined above,
cycloalkyl, or
heteroaryl;
R² is OR⁶ wherein R⁶ is as defined above, or

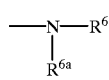

wherein R⁶ and R⁶ᵃ are the same or different and are as defined above for R⁶;
R³, R³ᵃ, R⁴, and R⁴ᵃ are the same or different and are
hydrogen,
fluorine,
alkyl,
—(CH₂)ₙ-aryl wherein n is an integer from 1 to 6,
—(CH₂)ₙ-heteroaryl wherein n is as defined above,
—(CH₂)ₙ-cycloalkyl wherein n is as defined above,
—(CH₂)ₚ—X—(CH₂)q-aryl wherein X is O, S, SO, SO₂, or NH, and p and q are each zero or an integer of 1 to 6, and the sum of p+q is not greater than six,
—(CH₂)ₚ—X—(CH₂)q-heteroaryl wherein X, p, and q are as defined above, or
—(CH₂)ₙ—R⁷ wherein R⁷ is
N-phthalimido,
N-2,3-naphthylimido, —OR⁶ wherein R⁶ is as defined above,

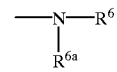

wherein R⁶ and R⁶ᵃ are the same or different and are as defined above for R⁶,
—SR⁶ wherein R⁶ is as defined above,

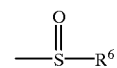

wherein R⁶ is as defined above,

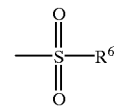

wherein R⁶ is as defined above,

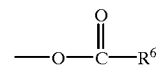

wherein R⁶ is as defined above,

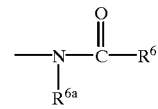

wherein R⁶ and R⁶ᵃ are the same or different and are as defined above for R⁶,

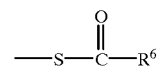

wherein R⁶ is as defined above,

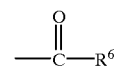

wherein R⁶ is as defined above,

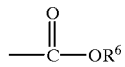

wherein R⁶ is as defined above, or

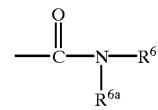

wherein R⁶ and R⁶ᵃ are the same or different and are as defined above for R⁶, and
n is as defined above;
R⁵ is OH, SH, or OR⁵ᵃ wherein R⁵ᵃ is alkyl, arylalkyl, cycloalkyl, or acyloxymethyl; with the proviso that R³, $R^{3a}$, $R^4$, and $R^{4a}$ are hydrogen or at least one of $R^3$, $R^{3a}$, $R^4$, or $R^{4a}$ is fluorine; with the further proviso that A and Q are not both phenyl; with the further proviso that when the atom to which R or $R^1$ is attached is nitrogen, R or $R^1$ is not halogen; and with the further proviso that Q may optionally be substituted on carbon with fluorine;

and corresponding isomers thereof; or a pharmaceutically acceptable salt thereof.

A second aspect of the present invention is a compound of Formula II

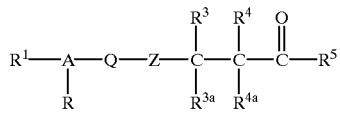

wherein A is

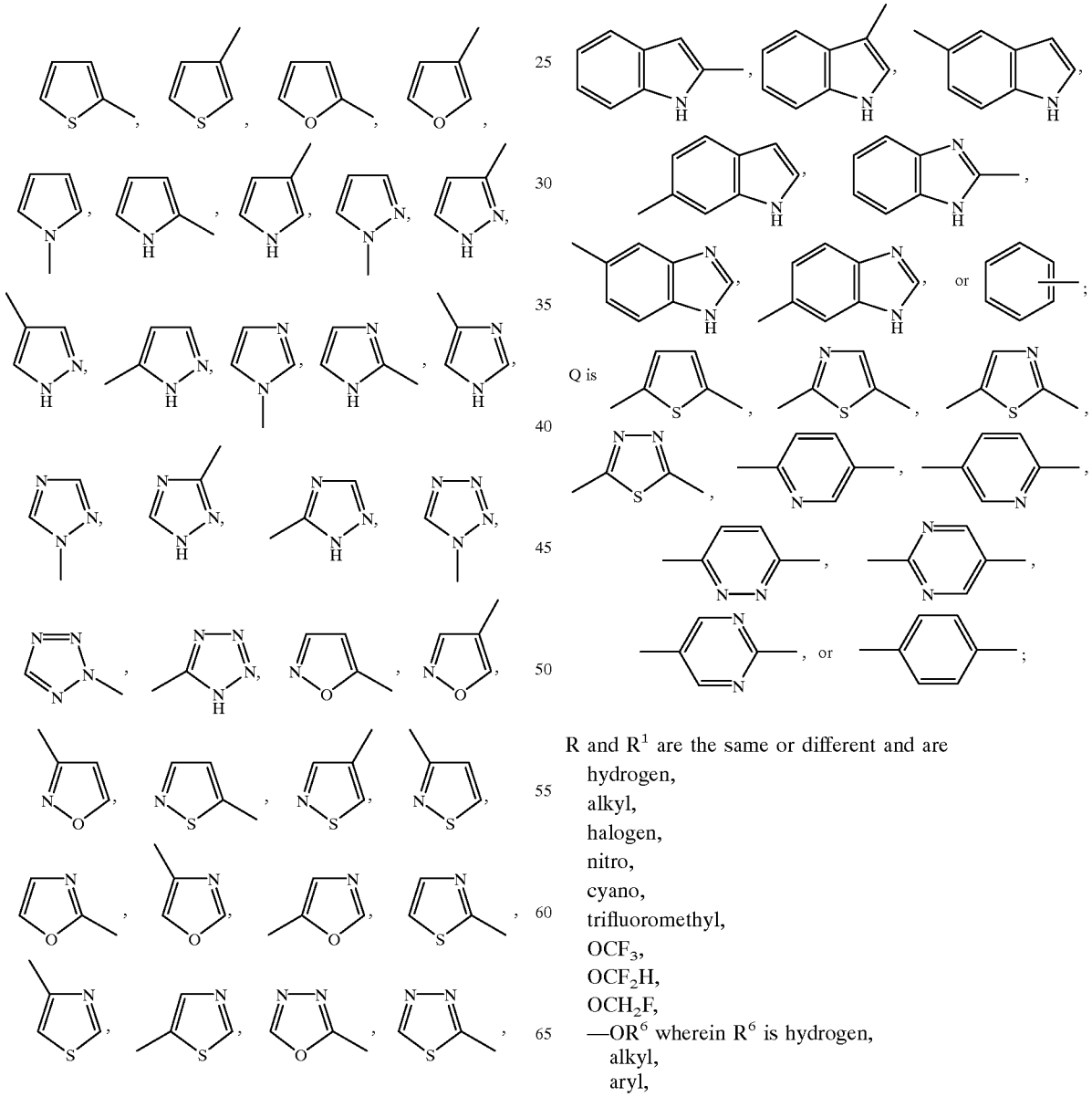

R and $R^1$ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
  alkyl,
  aryl, arylalkyl,
heteroaryl, or
cycloalkyl,

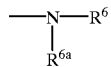

wherein $R^6$ and $R^{6a}$ are the same or different and are as defined above for $R^6$,

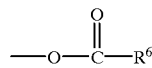

wherein $R^6$ is as defined above,

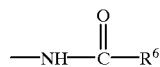

wherein $R^6$ is as defined above,

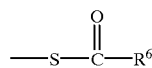

wherein $R^6$ is as defined above,
—$SR^6$ wherein $R^6$ is as defined above,

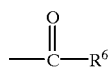

wherein $R^6$ is as defined above,
—$CH_2$—$OR^6$ wherein $R^6$ is as defined above,

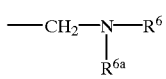

wherein $R^6$ and $R^{6a}$ are the same or different and are as defined above for $R^6$,

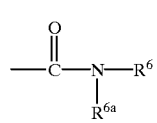

wherein $R^6$ and $R^{6a}$ are the same or different and are as defined above for $R^6$,

wherein $R^6$ is as defined above,

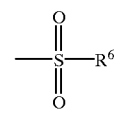

wherein $R^6$ is as defined above,
cycloalkyl, or
heteroaryl;

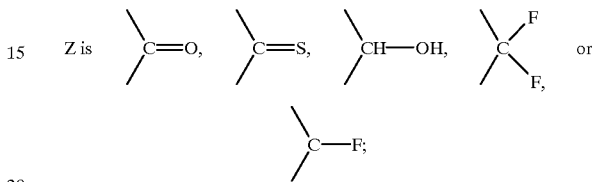

$R^3$, $R^{3a}$, $R^4$, and $R^{4a}$ are the same or different and are
hydrogen,
fluorine,
alkyl,
—$(CH_2)_n$-aryl wherein n is an integer from 1 to 6,
—$(CH_2)_n$-heteroaryl wherein n is as defined above,
—$(CH_2)_n$-cycloalkyl wherein n is as defined above,
—$(CH_2)_p$—X—$(CH_2)_q$-aryl wherein X is O, S, SO, $SO_2$, or NH, and p and q are each zero or an integer of 1 to 6, and the sum of p+q is not greater than six,
—$(CH_2)_p$—X—$(CH_2)_q$-heteroaryl wherein X, p, and q are as defined above, or —$(CH_2)_n$—$R^7$ wherein $R^7$ is
N-phthalimido,
N-2,3-naphthylimido,
—$OR^6$ wherein $R^6$ is as defined above,

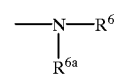

wherein $R^6$ and $R^{6a}$ are the same or different and are as defined above for $R^6$,
—$SR^6$ wherein $R^6$ is as defined above,

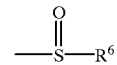

wherein $R^6$ is as defined above,

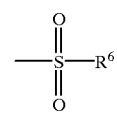

wherein $R^6$ is as defined above,

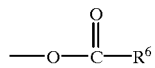

wherein $R^6$ is as defined above,

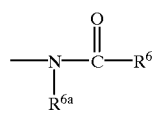

wherein $R^6$ is as defined above, defined above for $R^6$,

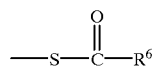

wherein $R^6$ is as defined above,

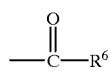

wherein $R^6$ is as defined above,

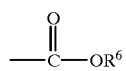

wherein $R^6$ is as defined above, or

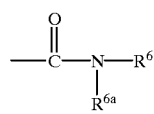

wherein $R^6$ and $R^{6a}$ are the same or different and are as defined above for $R^6$, and
n is as defined above;
$R^5$ is OH, SH, or $OR^{5a}$ wherein $R^{5a}$ is alkyl, arylalkyl, cycloalkyl, or acyloxymethyl;
with the proviso that at least one of $R^3$, $R^{3a}$, $R^4$, or $R^{4a}$ is fluorine; with the further proviso that A and Q are not both phenyl; with the further proviso that when the atom to which R or $R^1$ is attached is nitrogen, R or $R^1$ is not halogen; and with the further proviso that Q may optionally be substituted on carbon with fluorine; and corresponding isomers thereof; or a pharmaceutically acceptable salt thereof.

As matrix metalloproteinase inhibitors, the compounds of Formula I and Formula II are useful as agents for the treatment of multiple sclerosis. They are also useful as agents for the treatment of atherosclerotic plaque rupture, aortic aneurism, heart failure, restenosis, periodontal disease, corneal ulceration, treatment of burns, decubital ulcers, wound repair, cancer metastasis, tumor angiogenesis, inflammation, pain, arthritis, osteoporosis, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formulas I or II in unit dosage form in the treatment methods mentioned above. Finally, the present invention is directed to methods for production of compounds of Formula I or II.

DETAILED DESCRIPTION OF THE INVENTION

In the compounds of Formula I and Formula II, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, $SO_3H$, CHO,

as defined above for alkyl,

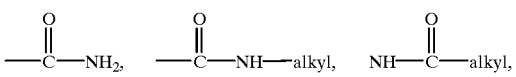

as defined above for alkyl,

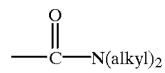

as defined above for alkyl, $—(CH_2)_n2—NH_2$ wherein $n^2$ is an integer of 1 to 5, $—(CH_2)_n2—NH$-alkyl as defined above for alkyl and $n^2$, $—CH_2)_n2—N(alkyl)_2$ as defined above for alkyl and $n^2$,

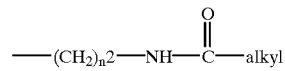

as defined above for alkyl, and $n^2$ and

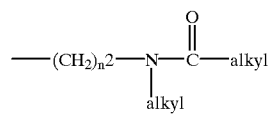

as defined above for alkyl and $n^2$.

The term "arylalkyl" means an aromatic radical attached to an alkyl radical wherein aryl and alkyl are as defined above for example benzyl, phenylethyl, 3-phenylpropyl, (4-chlorophenyl)methyl, and the like.

The term "acyloxymethyl" means a group of the formula

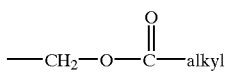

wherein alkyl is as defined above.

The term "heteroaryl" means a heteroaromatic radical and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl.

"Halogen" is fluorine, chlorine, bromine, or iodine.

"Alkali metal" is a metal in Group IA of the periodic table and includes, for example, lithium, sodium, potassium, and the like.

Some of the compounds of Formula I and Formula II wherein $R^5$ is OH are capable of further forming pharmaceutically acceptable carboxylic esters which are suitable as prodrugs. All of these carboxylic esters are within the scope of the present invention.

Pharmaceutically acceptable carboxylic esters of compounds of Formula I and Formula II include alkyl, cycloalkyl, arylalkyl, or acyloxymethyl esters.

The alkyl, cycloalkyl, and arylalkyl carboxylic esters of compounds of Formula I and Formula II can be prepared by methods known to one skilled in the art. For example, the corresponding carboxylic acids can be allowed to react directly with a suitable alcohol in the presence of a suitable acid catalyst to give the carboxylic esters. Alternatively, the carboxylic acids can be allowed to react with one of a number of suitable activating agents, which are known to one skilled in the art, followed by reaction with a suitable alcohol to give the carboxylic esters. Additionally for the 4-hydroxyimino-butyric acids of the present invention, the carboxylic acids can be allowed to cyclo-dehydrate using one of a number of methods known to one skilled in the art to give a cyclic 4,5-dihydro-6-oxo-6H-1,2-oxazine intermediate, which can be allowed to react with a suitable alcohol optionally in the presence of a suitable acid or base catalyst to give the carboxylic esters.

The acyloxymethyl esters of compounds of Formula I and Formula II can be prepared by methods known to one skilled in the art. For example, the corresponding carboxylic acids can be allowed to react first with a suitable base to give the carboxylate anion, followed by reaction with a carboxylic halomethyl ester, which can be obtained from commercial suppliers or prepared by methods known to one skilled in the art, optionally in the presence of a suitable agent to activate the carboxylic halomethyl ester, which are known to one skilled in the art, to give the acyloxymethyl esters.

Some of the compounds of Formula I and Formula II are capable of further forming both pharmaceutically acceptable acid addition and/or base salts. All of these forms are within the scope of the present invention.

Pharmaceutically acceptable acid addition salts of the compounds of Formula I and Formula II include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *J. of Pharma Sci.*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In the first embodiment of the invention, a preferred compound of Formula I is one wherein $R^2$ is OH or $OCH_3$; and $R^3$, $R^{3a}$, $R^4$, and $R^{4a}$ are hydrogen.

In the first embodiment of the invention, another preferred compound of Formula I is one wherein $R^2$ is OH or $OCH_3$; and at least one of $R^3$, $R^{3a}$, $R^4$, and $R^{4a}$ is fluorine.

Particularly valuable in the first embodiment of the invention is a compound selected from the group consisting of:
  4-[4-(5-Chloro-thiophen-2-yl)-phenyl]-4-hydroxyimino-butyric acid;

4-[4-(5-Chloro-thiophen-2-yl)-phenyl]-4-hydroxyimino-butyric acid, 2,2-dimethyl-propionyloxymethyl ester;
4-[4-(5-Chloro-thiophen-2-yl)-phenyl]-4-methoxyimino-butyric acid;
4-[4-(5-Bromo-thiophen-2-yl)-phenyl]-4-hydroxyimino-butyric acid;
4-[4-(5-Fluoro-thiophen-2-yl)-phenyl]-4-hydroxyimino-butyric acid;
4-[4-(5-Chloro-3-fluoro-thiophen-2-yl)-phenyl]-4-hydroxyimino-butyric acid;
4-Hydroxyimino4-[4-(5-trifluoromethyl-thiophen-2-yl)-phenyl]-butyric acid;
4-[5-(4-Chloro-phenyl)-thiophen-2-yl]-4-hydroxyimino-butyric acid;
4-[5-(4-Bromo-phenyl)-thiophen-2-yl]-4-hydroxyimino-butyric acid;
4-[5-(4-Fluoro-phenyl)thiophen-2-yl]-4-hydroxyimino-butyric acid;
4-[5-(4-Chloro-2-fluoro-phenyl)-thiophen-2-yl]-4-hydroxyimino-butyric acid;
4-[5-(4-Cyano-phenyl)-thiophen-2-yl]-4-hydroxyimino-butyric acid;
4-Hydroxyimino-4-[5-(4-trifluoromethyl-phenyl)-thiophen-2-yl)-butyric acid;
4-Hydroxyimino4-[5-4-methylsulfanyl-phenyl)thiophen-2-yl)-butyric acid;
4-[4-(5-Chloro-thiazol-2-yl)-phenyl]-4-hydroxyimino-butyric acid;
4-[4-(2-Chloro-thiazol-5-yl)-phenyl]-4-hydroxyimino-butyric acid;
4-[4-(5-Chloro-1,3,4-thiadiazol-2-yl)-phenyl]-4-hydroxyimino-butyric acid;
4-[5-(4-Chloro-phenyl)-pyrimidin-2-yl]-4-hydroxyimino-butyric acid;
4-[2-(4-Chloro-phenyl)-pyrimidin-5-yl]-4-hydroxyimino-butyric acid;
4-[4-(2-Chloro-pyrimidin-5-yl)-phenyl]-4-hydroxyimino-butyric acid;
4-[4-(5-Chloro-pyrimidin-2-yl)-phenyl]-4-hydroxyimino-butyric acid;
4-[5-(4-Chloro-phenyl)-pyrazin-2-yl]-4-hydroxyimino-butyric acid;
4-[4-(5-Chloro-pyrazin-2-yl)-phenyl]-4-hydroxyimino-butyric acid;
4-[4-(5-Fluoro-isoxazol-3-yl)-phenyl]-4-hydroxyimino-butyric acid;
4-[4-(3-Fluoro-isoxazol-5-yl)-phenyl]-4-hydroxyimino-butyric acid;
4-[4-(5-Fluoro-isothiazol-3-yl)-phenyl]-4-hydroxyimino-butyric acid;
4-[4-(3-Fluoro-isothiazol-5-yl)-phenyl]-4-hydroxyimino-butyric acid;
4-Hydroxyimino4-[4-(2-methoxy-pyrimidin-5-yl)-phenyl-butyric acid; and
4-Hydroxyimino4-(4-pyrazol-1-phenyl)-butyric acid.

Most particularly, valuable in the first embodiment of the invention is 4-[4-(5-Chloro-thiophen-2-yl)-phenyl]-4-hydroxyimino-butyric acid.

In the second embodiment of the invention, a preferred compound of Formula II is one wherein Z is

and
$R^3$ and $R^{3a}$ are fluorine.

In another second embodiment of the invention, a preferred compound of Formula II is one wherein Z is

and
$R^4$ and $R^{4a}$ are fluorine.

In a second embodiment of the invention, a more preferred compound of Formula II is one wherein Z is

and
$R^3$ is fluorine.

In a second embodiment of the invention, another more preferred compound of Formula II is one wherein Z is

and
$R^4$ is fluorine.

In another second embodiment of the invention, a preferred compound of Formula II is one wherein Z is

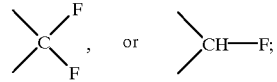

and
$R^3$ and $R^{3a}$ are fluorine.

In another second embodiment of the invention, a preferred compound of Formula II is one wherein Z is

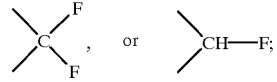

and

R⁴ and R⁴ᵃ are fluorine.

In another second embodiment of the invention, a preferred compound of Formula II is one wherein Z is

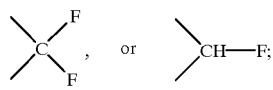

and

R³ is fluorine.

In another second embodiment of the invention, a preferred compound of Formula II is one wherein Z is

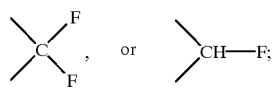

and

R⁴ is fluorine.

Particularly valuable in the second embodiment of the invention is 4-[4-(5-Chloro-thiophen-2-yl)-phenyl]-4-oxo-butyric acid; and corresponding isomers thereof; or a pharmaceutically acceptable salt thereof.

The compounds of Formula I and Formula II are valuable inhibitors of gelatinase A and/or stromelysin-1 and/or collagenase-3 (MMP-13). It has been shown previously that inhibitors of matrix metalloproteinases have efficacy in models of disease states like arthritis and metastasis that depend on modification of the extracellular matrix.

In vitro experiments were carried out which demonstrate the efficacy of compounds of Formula I and Formula II as potent and specific inhibitors of gelatinase A, collagenase-3, and stromelysin-1. Experiments were carried out with the catalytic domains of the proteinases. Table I shows the activity of Examples 1–3 versus MMP-13CD (collagenase-3 catalytic domain), MMP-2CD (gelatinase A catalytic domain), and MMP-3CD (stromelysin-1 catalytic domain). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*", *Biochemistry*, 1992;31:11231–11235).

TABLE 1

| Example | $IC_{50}(\mu M)$ | | |
| --- | --- | --- | --- |
| | MMP-2CD | MMP-3CD | MMP-13CD |
| 1 | 1.25 | 13 | 10.6 |
| 2 | 0.0639 | 0.298 | 1.1 |
| 3 | 0.014 | 0.105 | 0.12 |

The following list contains abbreviations and acronyms used within the schemes and text:

| | |
| --- | --- |
| Ac₂O | Acetic anhydride |
| CDI | 1,1'-Carbonyldiimidazole |
| CH₂Cl₂ | Dichloromethane |
| CNS | Central nervous system |
| EAE | Experimental autoimmune encephalomyelitis |
| MMP | Matrix metalloproteinase |
| VSMC | Vascular smooth muscle cell |
| EtOH | Ethanol |
| HCl | Hydrogen chloride |
| BOC | Tertiary-butoxycarbonyl |
| CBZ | Carbobenzyloxy |
| TBME | Tertiary-butyl methyl ether |
| $IC_{50}$ | Concentration of compound required to inhibit 50% of enzyme activity |
| KHMDS | Potassium hexamethyldisilazide |
| KOH | Potassium hydroxide |
| LiOH | Lithium hydroxide |
| MeOH | Methanol |
| n-BuLi | Normal-butyl lithium |
| THF | Tetrahydrofuran |
| TIMPs | Tissue inhibitors of metalloproteinases |
| H₂NOH | Hydroxylamine |
| H₂S | Hydrogen sulfide |
| Bu₃SnCl | Tributyltin chloride |
| AlCl₃ | Aluminum chloride |
| FeCl₃ | Ferric chloride |
| VCl₃ | Vanadium chloride |
| ZnCl₂ | Zinc chloride |
| MnCl₂ | Manganese chloride |
| CuBr | Copper (I) bromide |
| CuCN | Copper (I) cyanide |
| Na₂CO₃ | Sodium carbonate |
| KBr | Potassium bromide |
| K₂CO₃ | Potassium carbonate |
| NaBH₄ | Sodium borohydride |
| NaNO₂ | Sodium nitrite |
| NaOH | Sodium hydroxide |
| NaHCO₃ | Sodium bicarbonate |
| NaH | Sodium hydride |
| NBS | N-Bromosuccinimide |
| NFSI | N-Fluorodibenzenesulfonamide |
| TFA | Trifluoroacetic acid |
| TfOH | Trifluoromethanesulfonic acid |
| Tf₂O | Trifluoromethanesulfonic anhydride |
| HBr | Hydrogen bromide |
| LDA | Lithium diisopropylamide |
| NH₂NH₂ | Hydrazine |
| TEA (Et₃N) | Triethylamine |
| Me | Methyl |
| Et | Ethyl |
| nBu | Normal-butyl |
| tBu | Tertiary-butyl |
| Bn | Benzyl |
| PhNO₂ | Nitrobenzene |
| H₂O₂ | Hydrogen peroxide |
| (COCl)₂ | Oxalyl chloride |
| CCl₄ | Carbon tetrachloride |
| B(OiPr)₃ | Triisopropylborate |
| B(OMe)₃ | Trimethylborate |
| BF₃·OEt₂ | Boron triflouride etherate |
| Fe(acac)₃ | Iron(III)acetylacetonate |
| Pd | Palladium |
| PdCl₂(PPh₃)₂ | Bis(triphenylphosphine)palladium(II)chloride |
| Pd(PPh₃)₄ | Tetrakis(triphenylphosphine)palladium(0) |
| Ni | Nickel |
| Mg | Magnesium |
| Ph | Phenyl |
| DAST | Diethylamino sulfur trifluoride |
| DMF | Dimethylformamide |
| TMS-Cl | Chlorotrimethylsilane |
| CDCl₃ | Deuterated chloroform |
| DMSO | Dimethylsulfoxide |
| DMSO-d₆ | Deuterated dimethylsulfoxide |
| MgSO₄ | Magnesium sulfate |
| Na₂SO₄ | Sodium sulfate |
| p-TsOH | para-Toluenesulfonic acid |

| | |
|---|---|
| MsOH | Methanesulfonic acid |
| P$_4$S$_{10}$ | Phosphorus pentasulfide |
| PPA | Polyphosphoric acid |

Compounds of the formula H$_2$NR$^2$ can be obtained from commercial sources or prepared by methods generally known to one skilled in the art.

Compounds of Formulas I and II wherein R$^{3a}$ and R$^{4a}$ are hydrogen, Z is C=O, R$^5$ is OH, Q is not 1,3,4-thiadiazolyl, and A, R, R$^1$, R$^2$, R$^3$, and R$^4$ are as defined above can be synthesized by one of three general routes, as set forth in Scheme 1.

Route A involves reaction of a compound of Formula (2) with a suitable metallating agent such as, for example, n-butyl lithium, magnesium metal, and the like to generate an organolithium or organomagnesium salt in situ, followed by reaction of the salt with a suitable silylating agent such as, for example, chlorotrimethylsilane, to give a compound of Formula (3). A compound of Formula (3) can be allowed to react with a suitable metallating agent such as, for example, n-butyl lithium, magnesium(0), and the like to generate an organolithium or organomagnesium salt in situ, followed by reaction of the salt with a suitable metallating agent such as, for example, tri-(n-butyl)tin chloride, triisopropylborate, and the like to give a compound of Formula (4). A compound of Formula (4) can be coupled with a compound of Formula (5), which can be obtained from commercial sources or prepared by methods known to one skilled in the art, in the presence of a suitable catalyst such as, for example, tetrakis(triphenyl-phosphine)palladium(0), bis(triphenyl-phosphine)palladium(II)chloride, bis(triphenyl-phosphine)nickel(II)-chloride, [1,1'-bis(diphenyl-phosphino) ferrocene]nickel(II)-chloride, and the like, optionally in the presence of sodium carbonate in a suitable solvent system such as, for example, toluene/water, tetrahydrofuran, dimethyl-formamide, and the like at temperatures between about 25° C. and about 150° C. to give a compound of Formula (6). Alternatively, a compound of Formula (6) can be prepared from a compound of Formula (11), which can be obtained from commercial sources or prepared as described in Scheme 2, by using the methodology for preparing a compound of Formula (3) from a compound of Formula (2). A compound of Formula (6) can be allowed to react under Friedel-Crafts conditions with an acid chloride of Formula (7), prepared according to known methods such as, for example, as reported by Beckett, et al., *Synlett*, 1993:137, in the presence of a Lewis acid such as, for example, FeCl$_3$, AlCl$_3$, ZnCl$_2$, and the like either neat or in an inert solvent such as, for example, nitrobenzene. dichloromethane, and the like at temperatures between about −40° C. and about 120° C. to give a compound of Formula (8). Alternatively, a compound of Formula (8) can be prepared by allowing a compound of Formula (11) to react with a suitable metallating agent such as, for example, n-butyl lithium, magnesium(0), and the like in a suitable solvent such as, for example, diethyl ether, tert-butyl methyl ether, THF, and the like followed by reaction with a suitable Lewis Acid such as, for example, manganese(II)chloride, zinc(II) chloride, and the like optionally in the presence of lithium bromide and/or iron(III)acetyl-acetonate, followed by reaction with an acid chloride of the Formula (7). Alternatively, a compound of Formula (8) can be prepared by allowing a compound of Formula (11) to react with a suitable metallating agent such as, for example, n-butyl lithium, magnesium(0), and the like in a suitable solvent such as, for example, diethyl ether, tert-butyl methyl ether, THF, and the like, followed by reaction with trin-butyl)tin chloride to give a compound of Formula (12), which in turn can be allowed to react with a compound of Formula (7) in the presence of a suitable catalyst such as, for example, tetrakis(triphenylphosphine)palladium(0), and the like. A compound of Formula (8) can be deprotected using standard methodology known to one skilled in the art such as, for example, excess hydrogen chloride gas, trifluoroacetic acid, or alkali metal hydroxides such as sodium or potassium hydroxide, lithium hydrogen peroxide, and the like, in a suitable solvent such as, for example, dichloromethane, diethyl ether, aqueous methanol, aqueous THF, and the like followed by neutralization of acid or base salts, if any, followed by reaction of the resulting carboxylic acid intermediate with a compound of Formula (9), which can be obtained from commercial sources or prepared by methods known to one skilled in the art, optionally in the presence of a suitable base such as sodium or potassium carbonate in a suitable solvent such as ethanol, THF, acetic acid, and the like to give a compound of Formula (10).

Route B involves reaction of a compound of Formula (6), prepared according to Route A, with a suitable acylating agent such as, for example, succinic anhydride under Friedel-Crafts conditions such as those described for Route A to give a compound of Formula (13). A compound of Formula (13) can be allowed to react with a compound of Formula (9) under conditions such as those described for Route A to give a compound of Formula (14). Alternatively, a compound of Formula (6) can be allowed to react with a suitable acylating agent such as, for example, 3-carbomethoxypropionyl chloride and the like under Friedel-Crafts conditions such as those described for Route A to give a compound of Formula (15). Alternatively, a compound of Formula (15) can be prepared by allowing a compound of Formula (11) to react with a suitable metallating agent such as, for example, n-butyl lithium or magnesium(0) in a suitable solvent such as, for example, diethyl ether, tert-butyl methyl ether, THF, and the like followed by reaction with a suitable Lewis Acid such as, for example, manganese(II)-chloride, zinc(II)chloride, and the like optionally in the presence of lithium bromide and/or iron(III)acetylacetonate, followed by reaction with a suitable acid chloride such as, for example, 3-carbomethoxypropionyl chloride and the like. Alternatively, a compound of Formula (15) can be prepared by allowing a compound of Formula (12) to react with a suitable acid chloride such as, for example, 3-carbomethoxypropionyl chloride and the like in the presence of a suitable catalyst such as, for example, tetrakis(triphenylphosphine)palladium(0), and the like. A compound of Formula (15) can be deprotected using standard methodology such as that described for Route A followed by reaction of the resulting carboxylic acid intermediate with a compound of Formula (9) under conditions such as those described for Route A to give a compound of Formula (14).

Route C involves reaction of a compound of Formula (3), prepared according to Route A, under Friedel-Crafts conditions, such as those described for Route A, with an acid chloride of Formula (7) to give a compound of Formula (16). Alternatively, a compound of Formula (16) can be prepared by reacting a compound of Formula (19), which may be obtained from commercial sources or prepared by standard methods known to one skilled in the art, with a compound of Formula (7) under Friedel-Crafts conditions such as those described for Route A. A compound of Formula (16) can be coupled with a compound of Formula (18), which may be obtained from commercial sources or prepared by allowing a compound of Formula (17) to react with a suitable metallating agent such as, for example, n-butyl lithium, magnesium(0), and the like to generate an organolithium or organomagnesium salt in situ, followed by reaction of the salt with a suitable metallating agent such as, for example, tri-(n-butyl)tin chloride, triisopropylborate, and the like, in the presence of a suitable catalyst such as, for example, tetrakis(triphenylphosphine)palladium(0), bis(triphenylphosphine)palladium(II)chloride, bis(triphenylphosphine) nickel(II)chloride, [1,1'-bis(diphenylphosphino)ferrocene] nickel(II)chloride, and the like optionally in the presence of sodium carbonate in a suitable solvent system such as, for example, toluene/water, tetrahydrofuran, dimethylformamide, and the like at temperatures between about 25° C. and about 150° C. to give a compound of Formula (8). A compound of Formula (8) can be reacted using conditions such as those described for Route A to give a compound of Formula (10).

Alternatively, a compound of Formula (3) can be allowed to react with a suitable acylating agent such as, for example, 3-carbomethoxypropionyl chloride and the like under Friedel-Crafts conditions such as those described for Route A to give a compound of Formula (20). Alternatively, a compound of Formula (20) can be prepared by reacting a compound of Formula (19) with a suitable acylating agent such as, for example, 3-carbomethoxypropionyl chloride and the like under Friedel-Crafts conditions such as those described for Route A. A compound of Formula (20) can be coupled with a compound of Formula (18) using the conditions described previously for Route C to give a compound of Formula (15). A compound of Formula (15) can be reacted using conditions such as those described for Route A to give a compound of Formula (14).

Compounds of Formulas I and II wherein $R^{3a}$ and $R^{4a}$ are hydrogen, Z is C=O, $R^5$ is OH, Q is not 1,3,4-thiadiazolyl, and A, R, $R^1$, $R^2$, $R^3$, and $R^4$ are as defined above can be synthesized according to the sequence described in Scheme 2.

In Scheme 2, a compound of Formula (21), which can be obtained from commercial sources or prepared by methods known to one skilled in the art, can be allowed to react with a suitable metallating agent such as, for example, n-butyl lithium, magnesium(0), and the like to generate an organolithium or organomagnesium salt in situ, followed by reaction of the salt with a suitable metallating agent such as, for example, tri-(n-butyl)tin chloride, triisopropylborate, and the like to give a compound of Formula (22). A compound of Formula (22) can be coupled with a compound of Formula (17) in the presence of a suitable catalyst such as, for example, tetrakis(triphenylphosphine)palladium(0), bis (triphenylphosphine)palladium(II)chloride, bis (triphenylphosphine)nickel(II) chloride, [1,1'-bis (diphenylphosphino)ferrocene]nickel(II)chloride, and the like optionally in the presence of sodium carbonate in a suitable solvent system such as, for example, toluene/water, tetrahydrofuran, dimethylformamide, and the like at temperatures between about 25° C. and about 150° C. to give a compound of Formula (23). Alternatively, a compound of Formula (23) can be prepared by coupling a compound of Formula (2 1) with a compound of Formula (18) using conditions described previously. A compound of Formula (23) can be reduced to give a compound of Formula (24) using standard conditions known to one skilled in the art. Alternatively, a compound of Formula (25), which can be obtained from commercial sources or prepared by methods known to one skilled in the art, can be coupled with a compound of Formula (18) using conditions such as those described previously to give a compound of Formula (27), which can be deprotected using standard conditions known to one skilled in the art to give a compound of Formula (24). Alternatively, a compound of Formula (25) can be allowed to react with a suitable metallating agent such as, for example, n-butyl lithium, magnesium(0), and the like to generate an organolithium or organomagnesium salt in situ, followed by reaction of the salt with a suitable metallating agent such as, for example, tri-(n-butyl)tin chloride, triisopropylborate, and the like to give a compound of Formula (26), which can be coupled with a compound of Formula (17) using conditions such as those described previously to give a compound of Formula (27), which can be deprotected to give a compound of Formula (24) as described previously. A compound of Formula (24) can be reacted with a nitrite-based oxidizing agent (i.e., Sandmeyer reaction conditions) followed by a suitable source of halogen such as, for example, copper(II)chloride, copper(II) bromide, potassium iodide/HCl, and the like to give a compound of Formula (11). Alternatively, a compound of Formula (11) can be prepared by coupling a compound of Formula (18) with a compound of Formula (29), which can be prepared by reacting a compound of Formula (28) with trifluoromethanesulfonic anhydride, in the presence of a suitable catalyst such as, for example, tetrakis (triphenylphosphine)palladium(0), bis(triphenyl-phosphine) palladium(II)chloride, bis(triphenylphosphine)nickel(II) chloride, [1,1'-bis(diphenylphosphino)ferrocene]nickel(II) chloride, and the like optionally in the presence of sodium carbonate in a suitable solvent system such as, for example, toluene/water, tetrahydrofuran, dimethylformamide, and the like at temperatures between about 25° C. and about 150° C. A compound of Formula (11) can be converted to compounds of Formulas (10) and (14) according to the procedures described for Scheme 1, Routes A and B, respectively.

Compounds of Formulas I and II wherein $R^{3a}$ and $R^{4a}$ are hydrogen, Z is C=O, $R^5$ is OH, Q is 1,3,4-thiadiazolyl, and A, R, $R^1$, $R^2$, $R^3$, and $R^4$ are as defined above can be synthesized according to the two routes described in Scheme 3.

Route A involves reaction of a compound of Formula (30), which can be obtained from commercial sources or prepared according to methods known to one skilled in the art, with hydrazine in a suitable solvent such as, for example, ethanol, THF, and the like at temperatures between about 0° C. and about reflux to give a compound of Formula (31). A compound of Formula (31) can be reacted with a suitable sulfurating agent such as, for example, $P_4S_{10}$ and the like to give a compound of Formula (32). A compound of Formula (32) can be reacted with a suitable acylating agent such as, for example, 2-oxoglutarate, dimethyl ester in the presence of a suitable base such as, for example, triethylamine, pyridine and the like to give a compound of Formula (33). A compound of Formula (33) can be cyclized under acidic conditions such as, for example, in the presence of polyphosphoric acid, phenol and the like at temperatures between about 25° C. and about 150° C. to give a compound of Formula (34). A compound of Formula (34) can be deprotected and the resulting carboxylic acid reacted with a compound of Formula (9) using conditions described for Scheme 1, Route A to give a compound of Formula (35).

Route B involves reaction of a compound of Formula (36), which can be obtained from commercial sources or prepared according to methods known to one skilled in the art, with a thiosemicarbazide (37) in the presence of a suitable acid catalyst such as, for example, p-TsOH, MsOH, Amberlyst 15, and the like under dehydrating conditions such as, for example, in benzene, toluene, and the like at about reflux over a Dean-Stark trap, or in the presence of anhydrous $MgSO_4$, activated 3 angstrom molecular sieves, and the like at temperatures between about 0° C. and about reflux to give a compound of Formula (38). A compound of Formula (38) can be oxidatively cyclized using a suitable agent such as, for example, acetic anhydride and the like to give a compound of Formula (39). A compound of Formula (39) can be reacted with a suitable nitrite such as, for example, sodium nitrite, potassium nitrite, and the like followed by reaction with a suitable halogen source such as copper(l)chloride, copper(I)bromide, potassium iodide/HCl, and the like to give a compound of Formula (40). A compound of Formula (40) can be reacted with a suitable metallating agent such as, for example, n-butyl lithium, magnesium metal, and the like to generate an organolithium or organomagnesium salt in situ, followed by reaction of the salt with a suitable silylating agent such as, for example, chlorotrimethylsilane, and the like, to give a compound of Formula (41). A compound of Formula (41) can be allowed to react under Friedel-Crafts conditions, such as those described for Scheme 1, Route A, with an acid chloride of Formula (7) to give a compound of Formula (42). A compound of Formula (42) can be deprotected and the resulting carboxylic acid reacted with a compound of Formula (9) according to Scheme 1, Route A to give a compound of Formula (43). Alternatively, a compound of Formula (41) can be allowed to react under Friedel-Crafts conditions, such as those described for Scheme 1, Route A, with a suitable acid chloride such as, for example, 3-carbomethoxypropionyl chloride and the like to give a compound of Formula (34), which can be converted according to Route A to a compound of Formula (35).

Compounds of Formulas I and II wherein Z is C=O, $R^5$ is OH, and A, Q. R, $R^1$, $R^2$, $R^3$, $R^{3a}$, $R^4$, and $R^{4a}$ are as defined for Formula I can be synthesized as set forth in Scheme 4.

In Scheme 4, a compound of Formula (6) is allowed to react with a compound of Formula (44), which can be obtained from commercial sources or prepared according to methods known to one skilled in the art, under Friedel-Crafts conditions, such as those described for Scheme 1, Route A, to give a compound of Formula (45). Alternatively, a compound of Formula (45) can be prepared by reaction of a compound of Formula (11) with a suitable metallating agent followed by reaction with a suitable Lewis Acid according to the procedures described for Scheme 1, Route B, followed by reaction with a compound of Formula (44). Alternatively, a compound of Formula (45) can be prepared by reaction of a compound of Formula (12) with a compound of Formula (44) in the presence of suitable catalyst according to the procedures described for Scheme 1, Route B. A compound of Formula (45) can be reacted with a suitable non-nucleophilic base such as, for example, sodium hydride, lithium diisopropylamide, and the like in a suitable solvent such as, for example, THF, tert-butyl methyl ether, and the like at temperatures between about −100° C. and about 25° C. followed by reaction of the resulting enolate derivative with a compound of Formula (46), which can be obtained from commercial sources or prepared according to methods known to one skilled in the art, to give a compound of Formula (47). A compound of Formula (47) can be converted to a compound of Formula (48) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (48) can be reacted with a compound of Formula (9) according to those methods described for Scheme 1, Route A, to give a compound of Formula (49).

Alternatively, a compound of Formula (45) can be reacted with a suitable non-nucleophilic base under suitable conditions such as those described previously followed by reaction of the resulting enolate derivative with a compound of Formula (50), which can be obtained from commercial sources or prepared according to methods known to one skilled in the art, or NFSI for $R^{3a}$ equals fluorine to give a compound of Formula (51). A compound of Formula (51) can be reacted with a suitable non-nucleophilic base under suitable conditions such as those described previously followed by reaction with a compound of Formula (46) to give a compound of Formula (52). A compound of Formula (52) can be converted to a compound of Formula (53) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (53) can be reacted with a compound of Formula (9) according to those methods described for Scheme 1, Route A, to give a compound of Formula (54).

Alternatively, a compound of Formula (52) can be reacted with a suitable non-nucleophilic base under suitable conditions such as those described previously followed by reaction with a compound of Formula (55), which can be obtained from commercial sources or prepared according to methods known to one skilled in the art, or NFSI for $R^4$ equals fluorine to give a compound of Formula (56). A compound of Formula (56) can be converted to a compound of Formula (57) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (57) can be reacted with a compound of Formula (9) according to those methods described for Scheme 1, Route A, to give a compound of Formula (58).

Alternatively, a compound of Formula (56) can be reacted with a suitable non-nucleophilic base under suitable conditions such as those described previously followed by reaction with a compound of Formula (59), which can be obtained from commercial sources or prepared according to methods known to one skilled in the art, or NFSI for $R^{4a}$ equals fluorine to give a compound of Formula (60). A compound of Formula (60) can be converted to a compound of Formula (61) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (61) can be reacted with a compound of Formula (9) according to those methods described for Scheme 1, Route A, to give a compound of Formula (62).

Compounds of Formulas I and II wherein Z is C=O, $R^5$ is OH, and A, Q, R, $R^1$, $R^2$, $R^3$, $R^{3a}$, $R^4$, and $R^{4a}$ are as defined for Formula I can be synthesized as set forth in Scheme 5.

In Scheme 5, a compound of Formula (63) can be reacted with a suitable non-nucleophilic base under suitable conditions such as those described previously followed by reaction with a compound of Formula (59) or NFSI for $R^{4a}$ equals fluorine to give a compound of Formula (64). A compound of Formula (64) can be reacted with a suitable non-nucleophilic base under suitable conditions such as those described previously followed by reaction with a compound of Formula (65), which can be prepared by reacting a compound of Formula (6) with bromoacetyl chloride under Friedel-Crafts conditions such as those described for Scheme 1, Route A, to give a compound of Formula (66). A compound of Formula (66) can be converted to a compound of Formula (67) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (67) can be reacted with a compound of Formula (9) according to those methods described for Scheme 1, Route A, to give a compound of Formula (68).

Alternatively, a compound of Formula (66) can be reacted with a suitable non-nucleophilic base under suitable conditions such as those described previously followed by reaction with a compound of Formula (69), which can be obtained from commercial sources or prepared according to methods known to one skilled in the art, or NFSI for $R^3$ equals fluorine to give a compound of Formula (70). A compound of Formula (70) can be converted to a compound of Formula (71) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (71) can be reacted with a compound of Formula (9) according to those methods described for Scheme 1, Route A, to give a compound of Formula (72).

Alternatively, a compound of Formula (70) can be reacted with a suitable non-nucleophilic base under suitable conditions such as those described previously followed by reaction with a compound of Formula (50) or NFSI for $R^{3a}$ equals fluorine to give a compound of Formula (60). A compound of Formula (60) can be converted to a compound of Formula (61) which in turn can be converted to a compound of Formula (62) as described for Scheme 4.

Alternatively, a compound of Formula (63) can be reacted with a suitable non-nucleophilic base under suitable conditions such as those described previously followed by reaction with a compound of Formula (65) to give a compound of Formula (73). A compound of Formula (73) can be converted to a compound of Formula (74) by either deprotection followed by resolution of the resulting carboxylic acid into its stereoisomers according to methods known to one skilled in the art or by first a resolution into stereoisomers when $R^{11}$ is a chiral oxazolidinone, followed by deprotection according to methods known to one skilled in the art. A compound of Formula (74) can be reacted with a compound of Formula (9) according to those methods described for Scheme 1, Route A, to give a compound of Formula (75).

Compounds of Formulas I and II wherein $R^{3a}$ and $R^{4a}$ are hydrogen, Z is C=O, $R^5$ is OH, $A^1$ is as set forth in the scheme, and Q, R, $R^1$, $R^2$, $R^3$, and $R^4$ are as defined above can be synthesized as set forth in Scheme 6.

In Scheme 6, a fluorine-containing compound of Formula (76), which can be obtained from commercial sources or prepared according to methods known to one skilled in the art, can be converted to a silylated compound of Formula (77) according to the procedure described for Scheme 1, Route A. A compound of Formula (77) can be acylated with a compound of Formula (7) under Friedel-Crafts conditions according to the procedure described for Scheme 1, Route A, to give a compound of Formula (78). Alternatively, a compound of Formula (78) can be prepared by acylating a compound of Formula (82), which can be obtained from commercial sources or prepared according to methods known to one skilled in the art, with a compound of Formula (7) under Friedel-Crafts conditions according to the procedure described for Scheme 1, Route A. A compound of Formula (78) can be condensed with a compound of Formula (79), which can be obtained from commercial sources or prepared according to methods known to one skilled in the art, in the presence of a suitable base such as, for example, an alkali metal carbonate such as sodium, potassium, or cesium carbonate and the like or an alkali metal hydride such as sodium or potassium hydride and the like in a suitable solvent such as DMSO, DMF, diglyme and the like to give a compound of Formula (80). A compound of Formula (80) can be deprotected using standard methodology known to one skilled in the art such as, for example, excess hydrogen chloride gas, trifluoroacetic acid, or alkali metal hydroxides such as sodium or potassium hydroxide, or lithium hydrogen peroxide, and the like, in suitable solvents such as, for example, dichloromethane, diethyl ether, aqueous methanol, aqueous THF, and the like, followed by neutralization of acid or base salts, if any, followed by reaction of the resulting carboxylic acid intermediate with a compound of Formula (9) optionally in the presence of a suitable base such as sodium or potassium carbonate in a suitable solvent such as ethanol, THF, acetic acid, and the like to give a compound of Formula (81).

Alternatively, compounds of Formulas (77) and (82) can be acylated with a suitable acylating agent such as, for example, 3-carbomethoxypropionyl chloride and the like under Friedel-Crafts conditions such as those described for Route A to give a compound of Formula (83). A compound of Formula (83) can be condensed with a compound of Formula (79) using suitable conditions such as those describe previously to give a compound of Formula (84). A compound of Formula (84) can be deprotected according to conditions described previously and the resulting carboxylic acid condensed with a compound of Formula (9) according to conditions described in Scheme 1, Route A, to give a compound of Formula (85).

Compounds of Formula II wherein Z is CH(OH), C=S, CHF, or $CF_2$, $R^5$ is OH, and A, Q, R, $R^1$, $R^3$, $R^{3a}$, $R^4$, and $R^{4a}$ are as defined for Formula II can be synthesized as set forth in Scheme 7.

In Scheme 7, compounds of Formulas (8), (15), (34), (42), (47), (52), (56), (60), (66), (70), or (73) can be deprotected using standard methodology known to one skilled in the art such as, for example, excess hydrogen chloride gas, trifluoroacetic acid, or alkali metal hydroxides such as sodium or potassium hydroxide, or lithium hydrogen peroxide, and the like, in suitable solvents such as, for example, dichloromethane, diethyl ether, aqueous methanol, aqueous THF, and the like followed by neutralization of acid or base salts, if any, followed by reaction of the resulting carboxylic acid intermediate with a suitable hydride reducing agent such as, for example, sodium borohydride, lithium borohydride optionally in the presence of a suitable activating agent such as, for example, chlorotrimethylsilane, lithium tri-sec-butylborohydride, diisobutylaluminum hydride, and the like, or one of a number of chiral borohydride reagents which are known to one skilled in the art, and the like to give a compound of Formula (86). A compound of Formula (86) can be reacted with a suitable silylating agent such as, for example, chlorotrimethylsilane (excess) in the presence of a suitable catalyst such as, for example, imidazole and the like in a suitable solvent such as, for example, anhydrous dimethylformamide and the like to give the corresponding silyl alcohol-silyl ester, which can be fluorinated by reaction with a suitable reagent such as, for example, diethylaminosulfur trifluoride (DAST) and the like in a suitable solvent such as dichloromethane, chloroform and the like at temperatures between about −20° C. and about reflux to give a compound of Formula (87). Alternatively, compounds of Formulas (8), (15), (34), (42), (47), (52), (56), (60), (66), (70), or (73) can be reacted with a suitable fluorinating agent such as, for example, DAST and the like in a suitable solvent such as, for example, dichloromethane, chloroform and the like and the resulting gamma, gamma-difluoro product can be deprotected as described previously to give a compound of the Formula (88). Alternatively, compounds of Formulas (8), (15), (34), (42), (47), (52), (56), (60), (66), (70), or (73) can be deprotected as described previously and the resulting carboxylic acid can be reacted with a suitable sulfurating agent such as, for example, Lawesson's Reagent to give a compound of the Formula (89).

Compounds of Formulas I and II wherein $R^2$ is OH, $R^5$ is O—$R^{5a}$, and Z, A, Q, R, $R^1$, $R^2$, $R^3$, $R^{3a}$, $R^4$, $R^{4a}$, and $R^{5a}$ are as defined for Formula I can be synthesized as set forth in Scheme 8.

In Scheme 8, compounds of Formulas (10), (14), (35), (43), (49), (54), (58), (62), (68), (72), or (75) can be cyclo-dehydrated using a suitable catalyst such as, for example, p-toluenesulfonic acid, Amberlyst 15, and the like in a suitable solvent such as, for example, toluene, benzene, n-heptane, and the like using dehydrating methodology such as, for example, refluxing over a Dean-Stark trap or by using a dehydrating agent such as, for example, 3 angstrom molecular sieves, anhydrous magnesium sulfate, and the like to give a compound of Formula (90). A compound of Formula (90) can be condensed with a compound of Formula (91), which can be obtained from commercial sources or prepared according to methods known to one skilled in the art, in the presence of a suitable acid catalyst such as, for example, hydrogen chloride gas, p-toluenesulfonic acid, Amberlyst 15, and the like, or a suitable base catalyst such as, for example, sodium hydride and the like in a suitable solvent such as, for example, chloroform, dioxane, and the like at temperatures between about 25° C. and about reflux to give compounds of Formulas (92) and (93). Alternatively, compounds of Formulas (10), (14), (35), (43), (49), (54), (58), (62), (68), (72), (75), or IIa wherein $R^5$ is OH can be deprotonated with a suitable base such as, for example, sodium hydroxide, potassium hydroxide, sodium bicarbonate, and the like in a suitable solvent such as, for example, methanol, ethanol, 2-propanol, acetone, DMSO, and the like at temperatures between about 0° C. and about 25° C., and the resulting carboxylate salt can be reacted with a compound of Formula (94), wherein halo is chlorine, bromine, or iodine and which can be obtained from commercial sources or prepared according to methods known to one skilled in the art, optionally in the presence of a suitable catalyst such as, for example, sodium iodide, silver nitrate, and the like at temperatures between about 0° C. and about reflux to give the compounds of Formulas (95), (96), or (97) in the case of IIa.

Compounds of Formulas I and II wherein $R^5$ is SH or S—$R^{5a}$, and Z, A, Q, R, $R^1$, $R^2$, $R^3$, $R^{3a}$, $R^4$, $R^{4a}$, and $R^{5a}$ are as defined for Formula I can be synthesized as set forth in Scheme 9.

In Scheme 9, compounds of Formulas Ia or IIa wherein $R^5$ is OH are allowed to react with a suitable carboxylic acid activating agent such as, for example, 1,1'-carbonyldiimidazole, N,N'-dicyclohexylcarbodiimide, isobutyl chloroformate, and the like in a suitable solvent such as, for example, THF, tert-butyl methyl ether, dichloromethane, and the like at temperatures between about −20° C. and about reflux in the presence of or followed by the addition of a suitable source of sulfur such as, for example, hydrogen sulfide, sodium monohydrogen sulfide, and the like to give compounds of the Formulas (98) and (99), respectively. Compounds of Formulas (98) and (99) can be allowed to react with a compound of Formula (100), wherein halo is chlorine, bromine, or iodine and which can be obtained from commercial sources or prepared according to methods known to one skilled in the art, optionally in the presence of a suitable catalyst such as, for example, sodium iodide, silver nitrate, and the like at temperatures between about 0° C. and about reflux to give the compounds of Formulas (101) and (102), respectively.

Compounds of Formula $H_2NR^2$(9) can be obtained from commercial sources or prepared by methods generally known to one skilled in the art.

Examples of commercially available compounds which can be used in Schemes 1 or 2 include 2-bromo-5-nitropyridine, 5-bromo-2-nitropyridine, 3-amino-6-chloropyridazine, 2-amino-5-bromopyrimidine, 2-hydroxy-5-iodopyrimidine, 2,5-dibromothiophene, 2-bromo-5-nitrothiophene, 2-amino-5-bromo-thiazole hydrobromide, 2-bromo-5-nitrothiazole, 1,4-dibromobenzene, 4-bromophenol, and the like.

SCHEME 1

Route A:

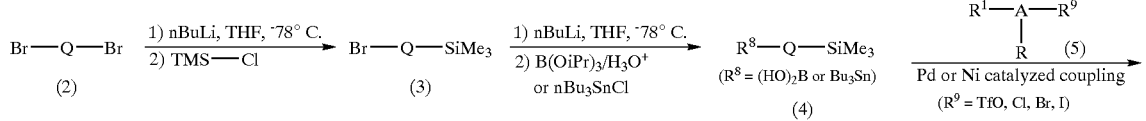

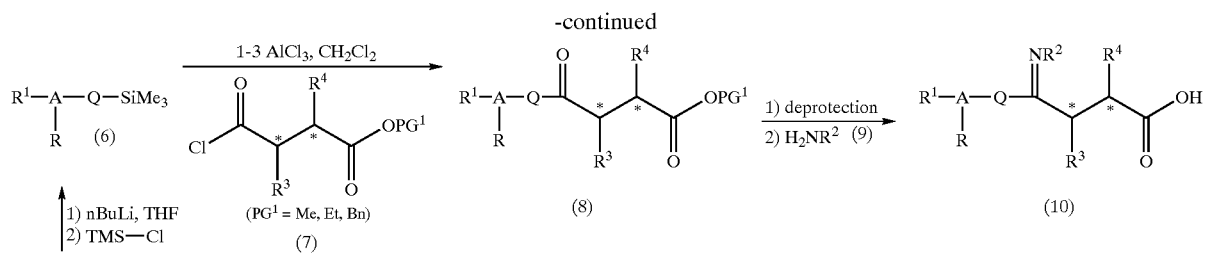
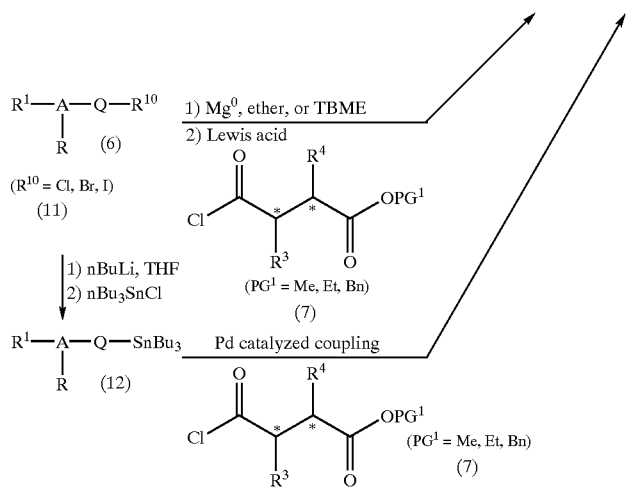
Route B
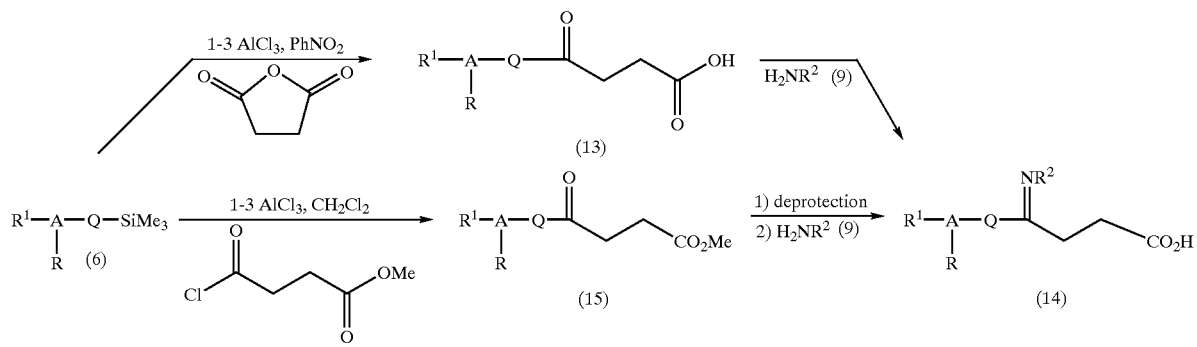
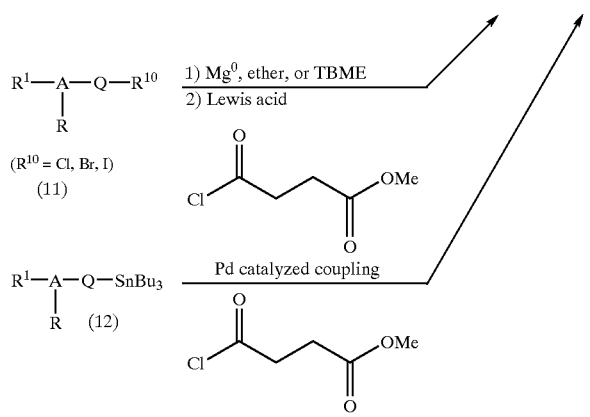

Route C:
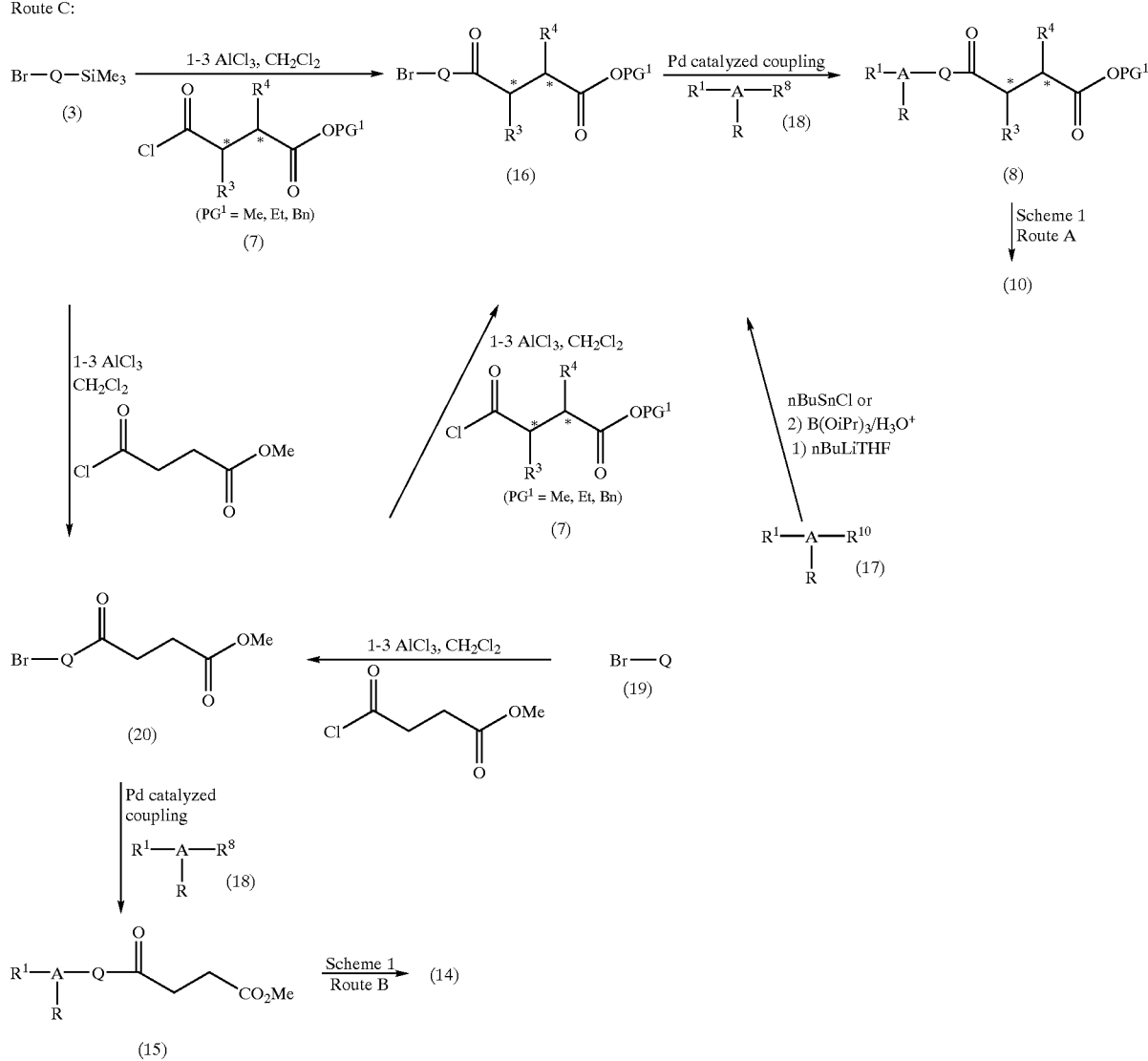
SCHEME 2
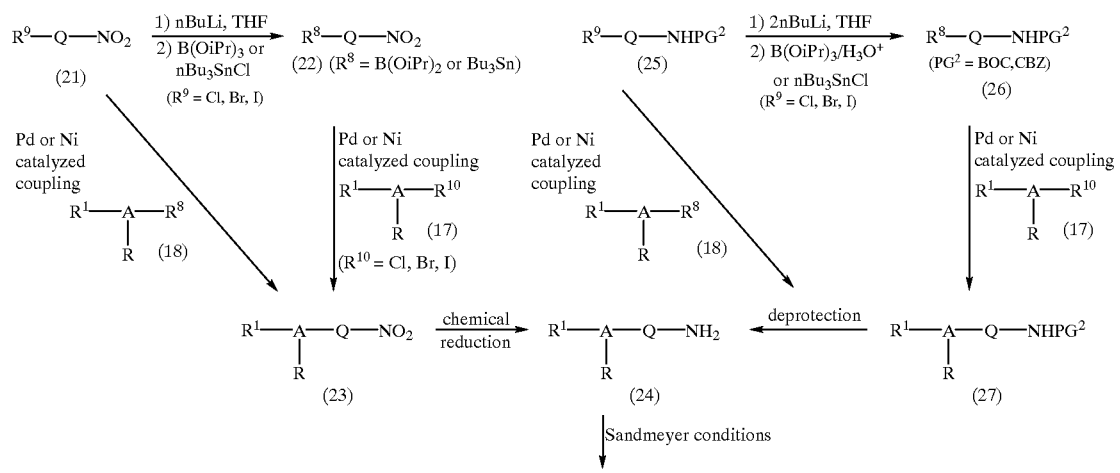

-continued
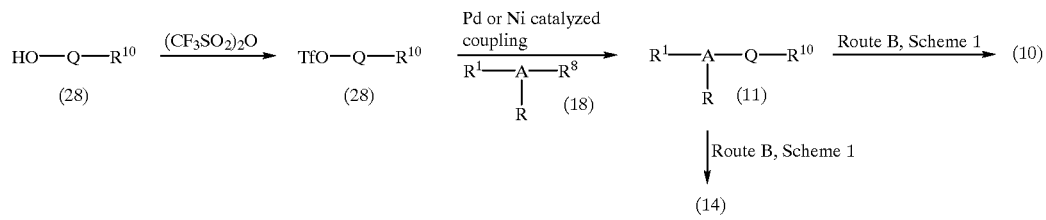
SCHEME 3
Route A:
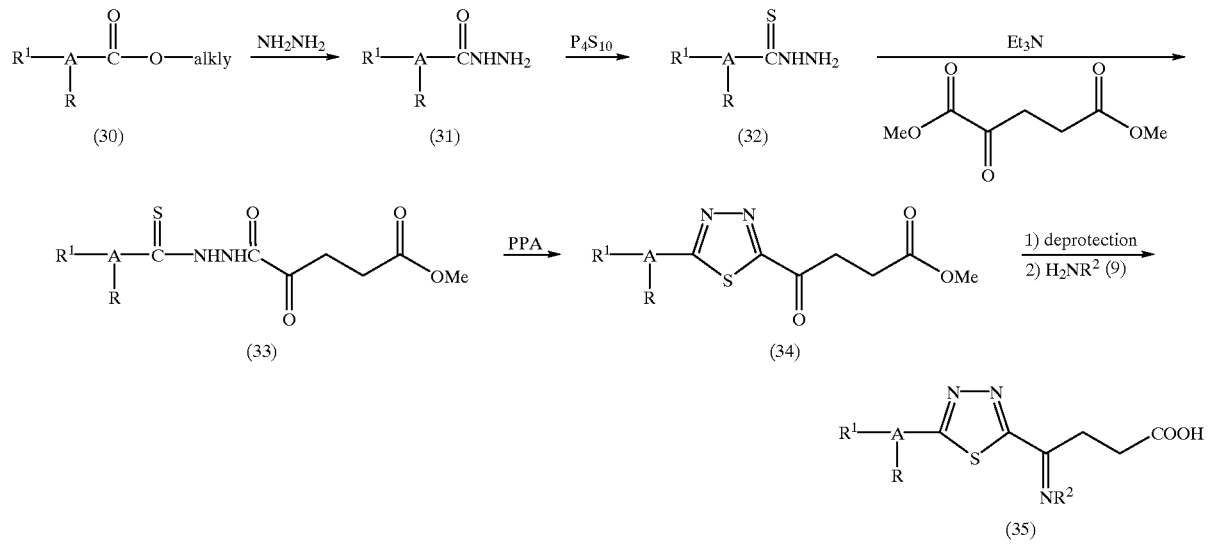
Route B:
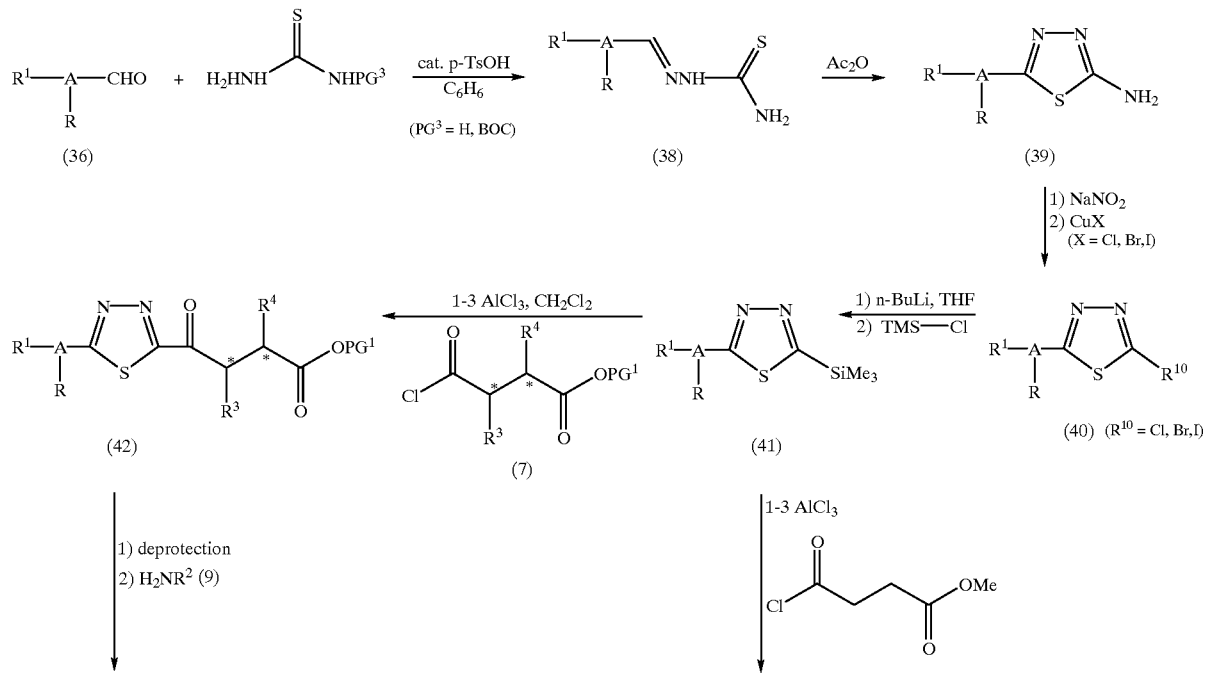

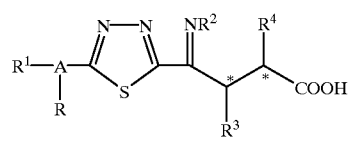
(43)
-continued
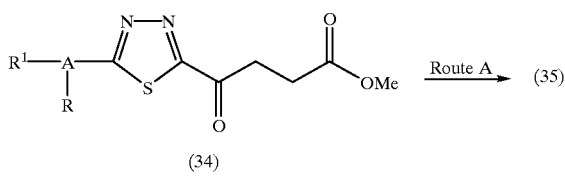
SCHEME 4
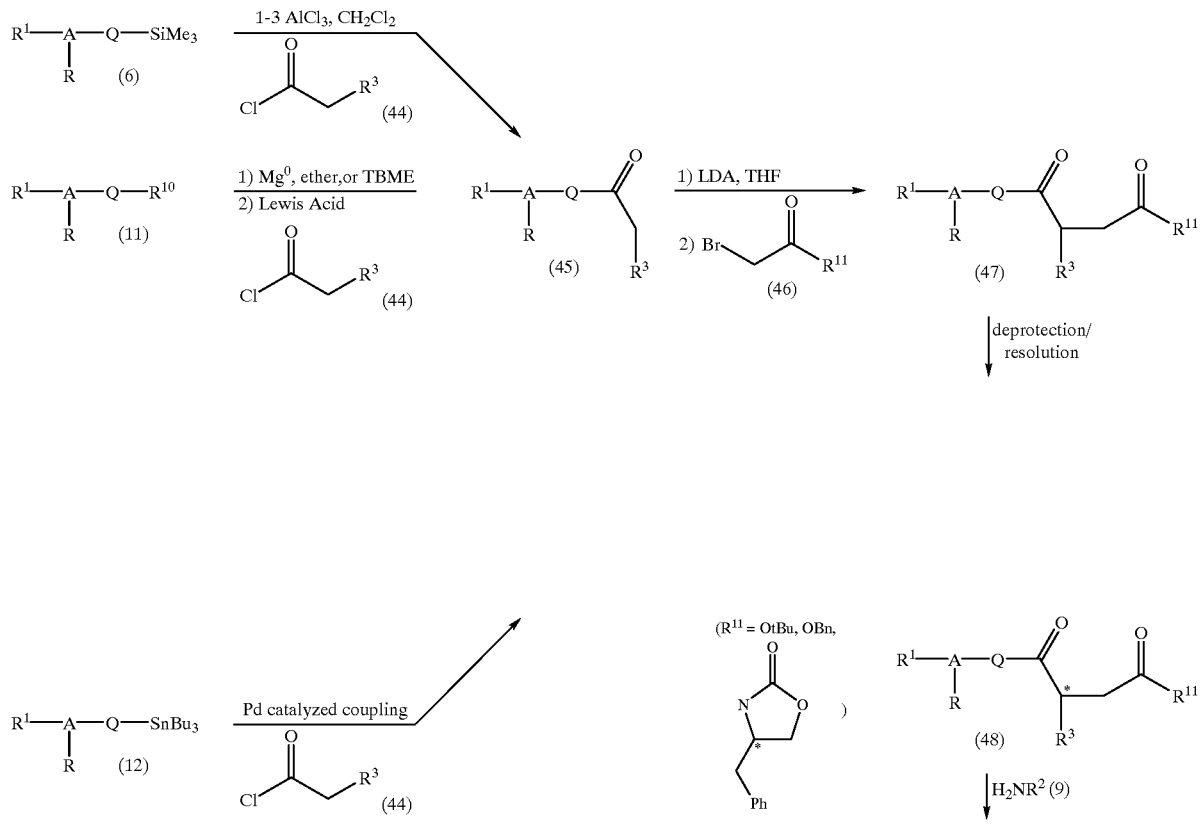
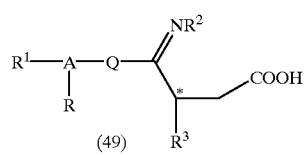

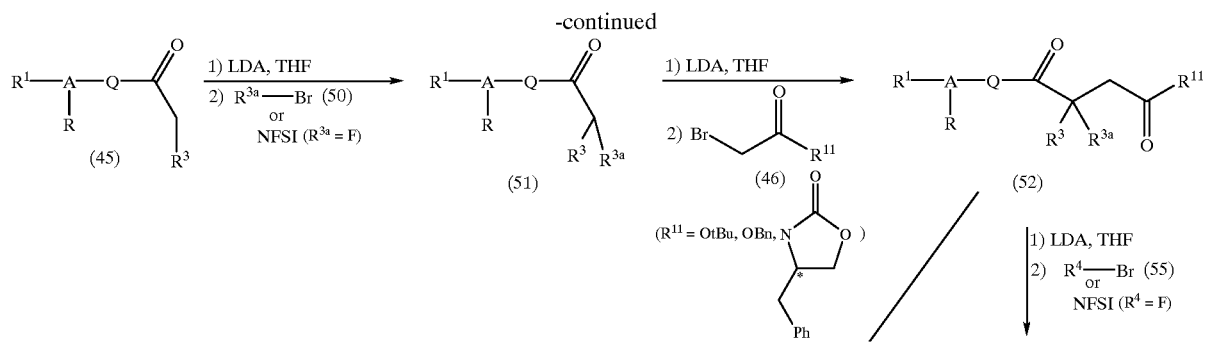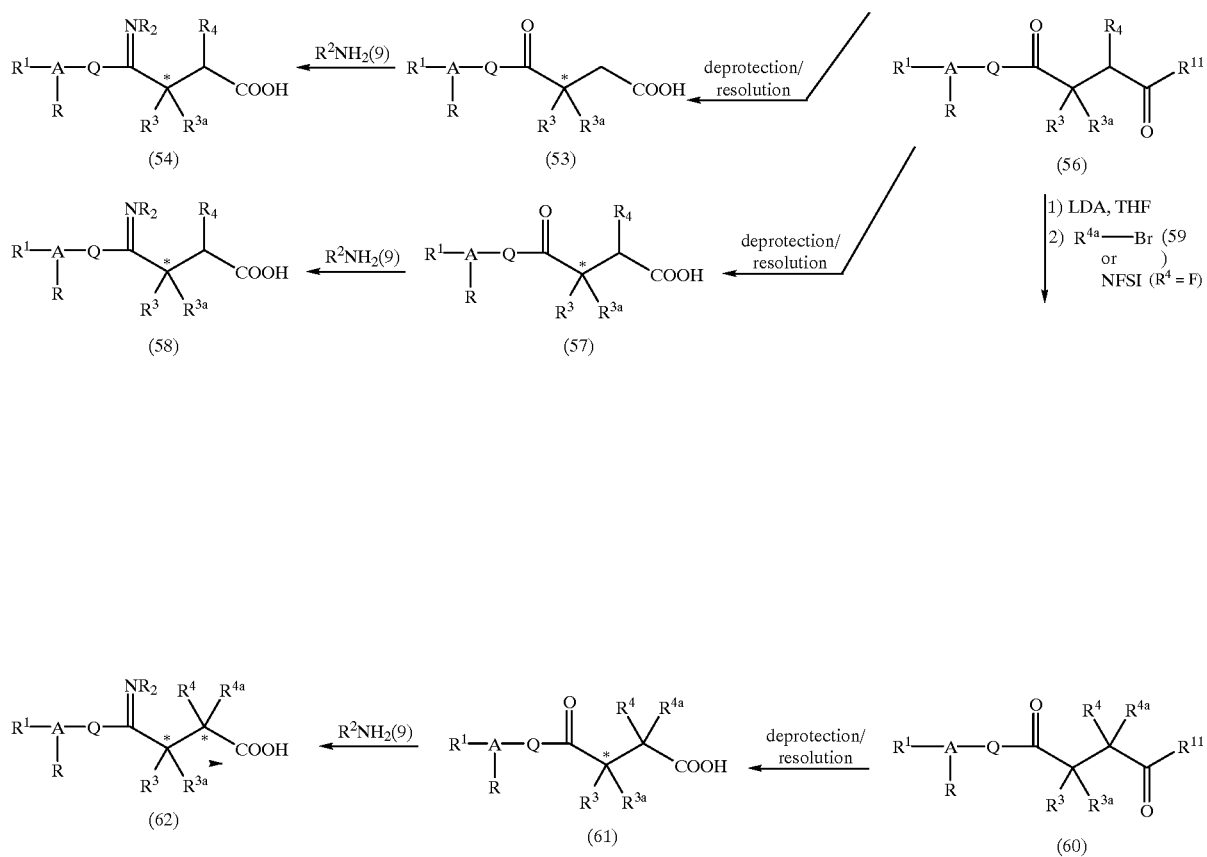

SCHEME 5
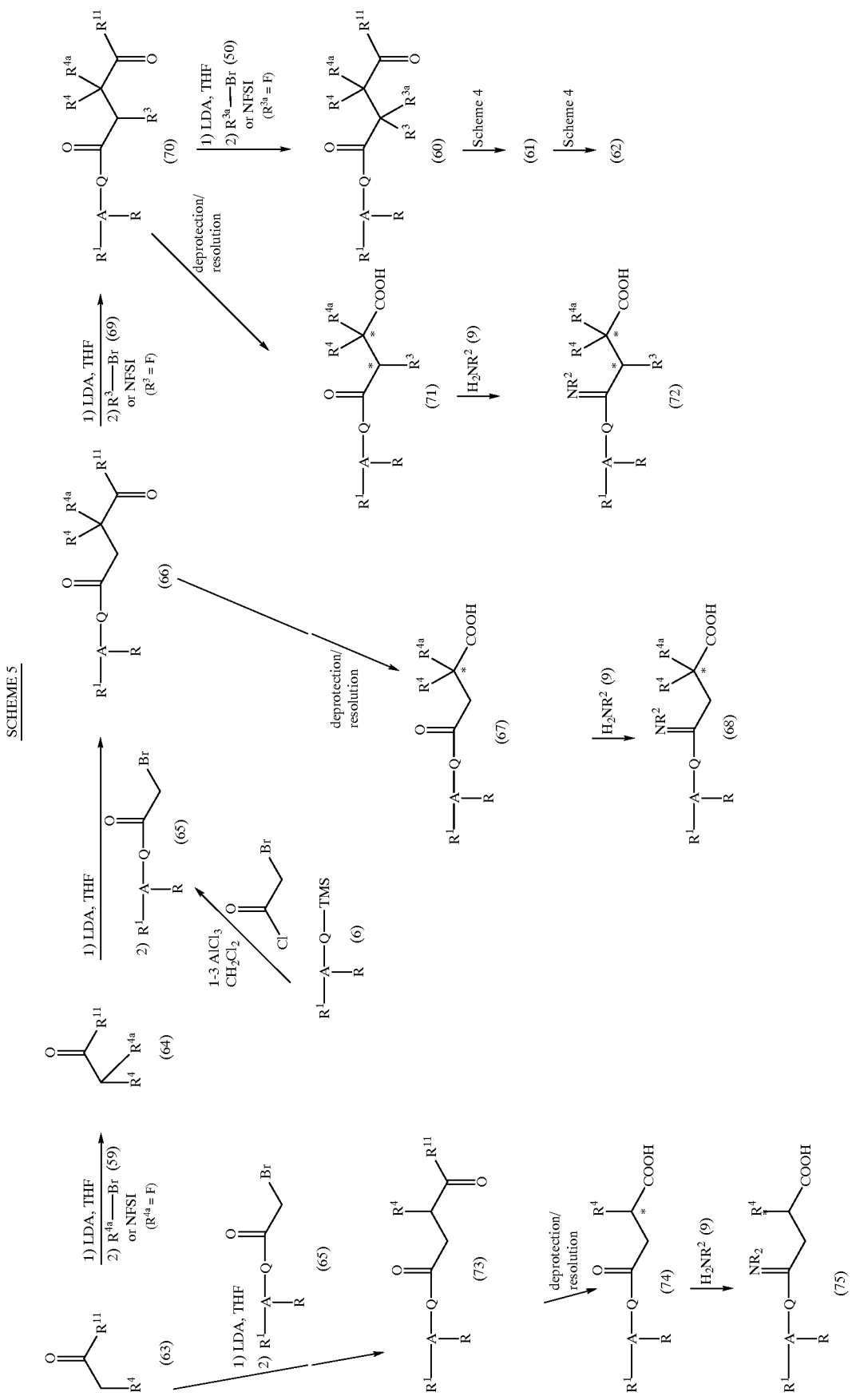

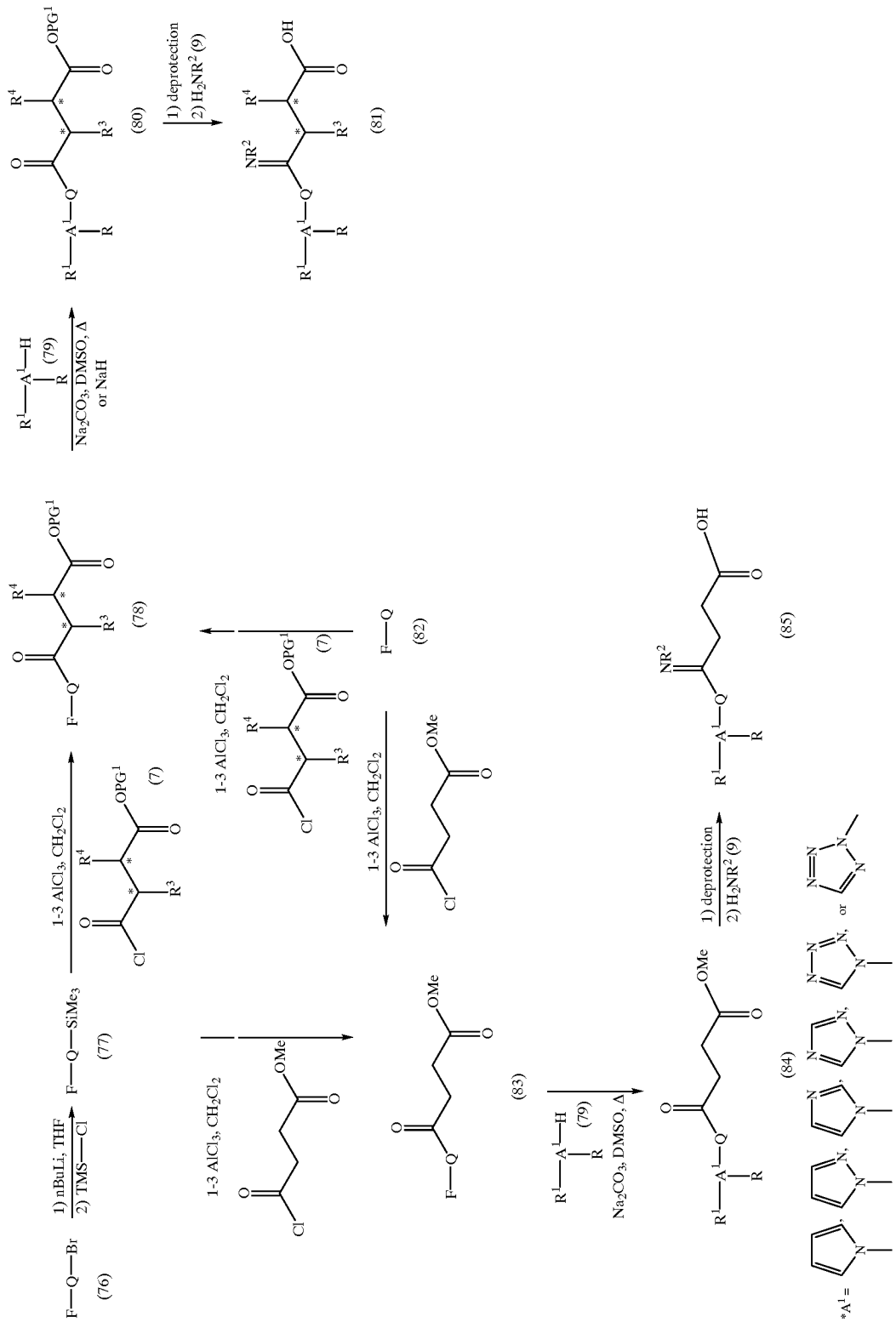

SCHEME 7
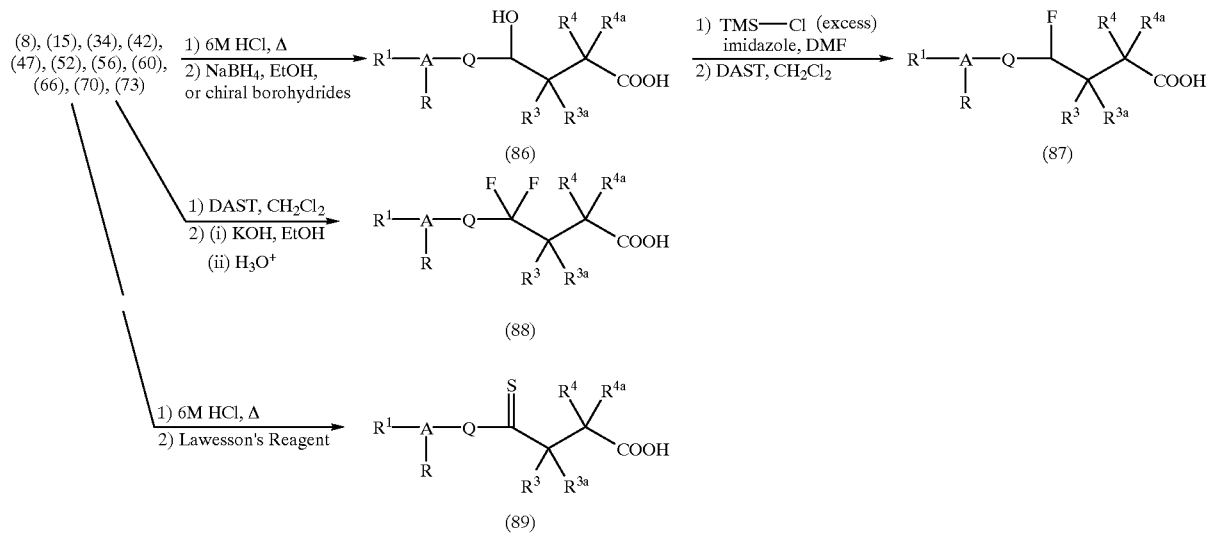
SCHEME 8
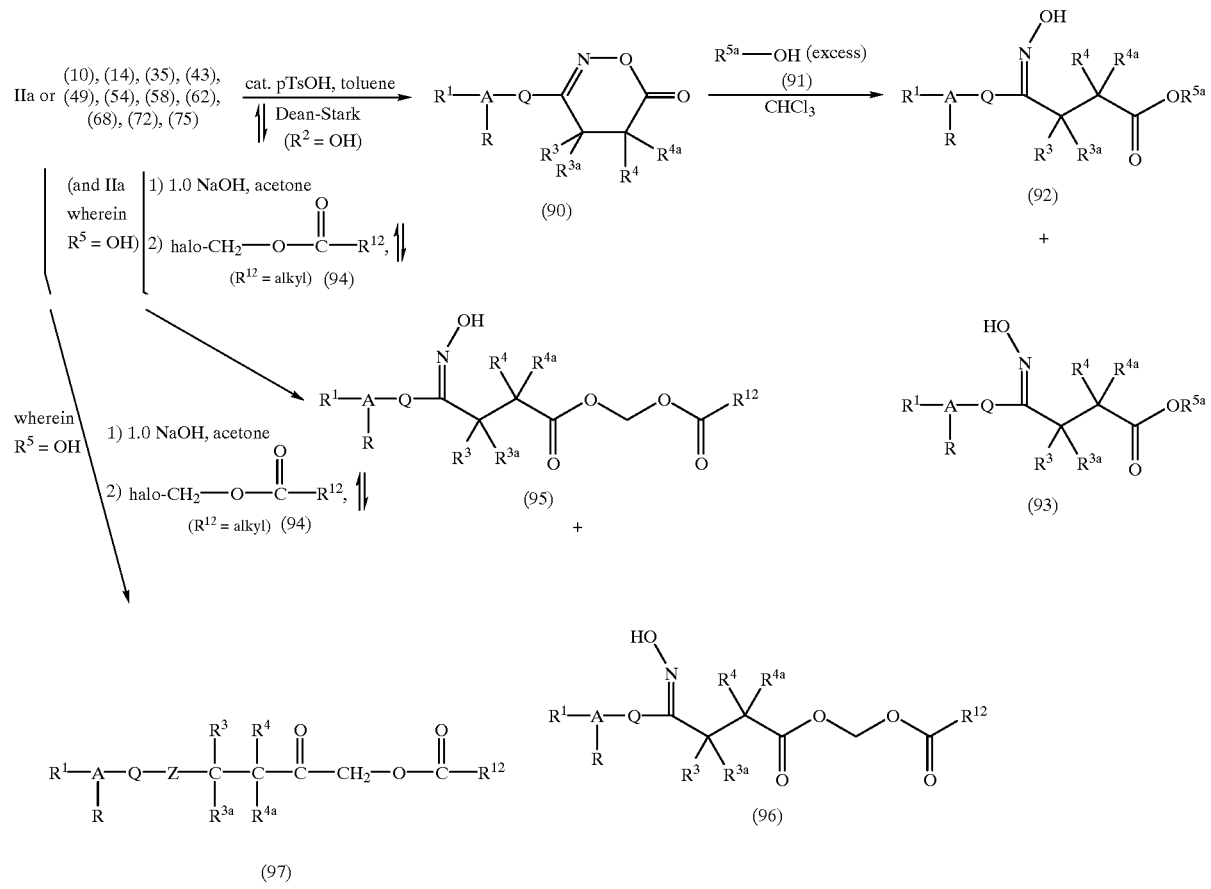

SCHEME 9

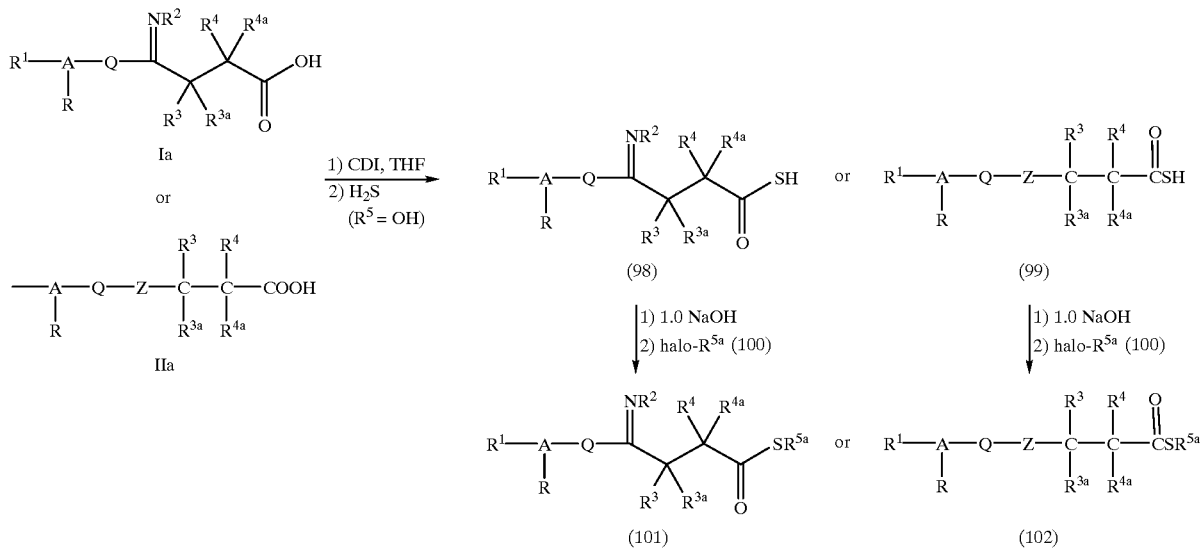

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or II or a corresponding pharmaceutically acceptable salt of a compound of Formula I or Formula II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% of the active compound. Suitable carriers are magnesium carbonate, magnesium stearate, talc, sugar, lactose, pectin, dextin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy, the compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

4-Hydroxyimino-4-(4-pyrazol-1-yl-phenyl)butyric Acid

To a stirred suspension of 4oxo-4(4-pyrazol-1-yl-phenyl) butyric acid (Sircar I., et al., *Journal of Medicinal Chemistry*, 1985;28:1405–13) (0.0277 g, 0.000113 mol) in absolute ethanol (0.55 mL) at room temperature was added potassium carbonate (0.010 g, 0.000072 mol) followed by a solution of hydroxylamine hydrochloride (0.010 g, 0.00014 mol) in water (0.25 mL), and the resulting mixture was stirred for 1 day. The volatiles were rotary evaporated. The residue was dissolved in methanol, silica gel (0.35 g, 230–400 mesh) was added, and the mixture was rotary evaporated to dryness. The residue was purified by chromatography on silica gel (6.0 g, 230–400 mesh) eluting with dichloromethane-methanol (12:1,25×5 mL) to give 0.0230 g of 4-hydroxyimino-4(4pyrazol-1-yl-phenyl)-butyric acid as an off-white solid; mp 128–130° C.

EXAMPLE 2

4-[4-(5-Chloro-thiophen-2-yl)-phenyl]-4-oxo-butyric Acid

Step (a) Preparation of 4-(4-Bromo-phenyl)-4-oxo-butyric Acid, Methyl Ester

To a stirred suspension of anhydrous aluminum chloride (26.9 g, 0.202 mol) in dichloromethane (415 mL) at 5° C. under nitrogen was added dropwise neat bromobenzene (10.0 mL, 0.0950 mol), and the mixture was stirred briefly. To the mixture was added dropwise a solution of 3-carbomethoxypropionyl chloride (12.9 mL, 0.105 mol) in dichloromethane (200 mL) over 70 minutes, and the mixture was allowed to slowly warm to room temperature. After 4 days, the mixture was recooled to 5° C. and quenched with the dropwise addition of water (600 mL). The organics were washed with additional water (200 mL), aqueous sodium bicarbonate, water, and brine. The organics were dried ($Na_2SO_4$), and rotary evaporated to an oil, which crystallized. The residue was dissolved in chloroform, and the solution was purified by chromatography on silica gel (435 g, 230–400 mesh), eluting with hexanes-acetone (9:1, 10×400 mL; 8:1, 7×400 mL),to give 21.2 g of 4-(4-bromo-phenyl)-4-oxo-butyric acid, methyl ester as an off-white solid; mp 49–51° C.

Step (b) Preparation of 4-[4-(5-Chloro-thiophen-2-yl)-phenyl]-4-oxo-butyric Acid, Methyl Ester A stirred mixture of 5-chloro-thiophene-2-boronic acid (5.15 g, 0.0317 mol), 4-(4-bromo-phenyl)-4-oxo-butyric acid, methyl ester (8.00 g, 0.0294 mol), and tetrakis (triphenylphosphine)palladium(0) (1.09 g, 0.00094 mol) in a two-phase mixture of toluene (62 mL) and 2.0 M aqueous sodium carbonate (31 mL, 0.062 mol) was heated at 70° C. for 20 hours and allowed to cool to room temperature. Additional 5-chloro-thiophene-2-boronic acid (0.369 g, 0.00227 mol) was added, and the mixture was reheated at 65° C. for 20 hours. The mixture was cooled to room temperature and filtered through Celite, eluting with dichloromethane. Filtrate and washings were combined, and the mixture was washed with 0.10 M aqueous sodium hydroxide (100 mL), 3% aqueous ammonium hydroxide (100 mL), water, and brine. The organics were dried ($Na_2SO_4$), and rotary evaporated to a solid. The residue was dissolved in chloroform. silica gel (101 g, 230–400 mesh) was added, and the mixture was rotary evaporated to dryness. The residue was purified by chromatography on silica gel (1450 g, 230–400 mesh), eluting with hexanes-acetone (12:1, 16×1L; 9:1, 12×1L) to give 6.04 g of 4-[4-(5-chloro-thiophen-2-yl)-phenyl]-4-oxo-butyric acid, methyl ester as a bright yellow solid; mp 117–118° C.

Step (c) Preparation of 4-[4-(5-Chloro-thiophen-2-yl)-phenyl]-4-oxo-butyric Acid A mixture of 4-[4-(5-chloro-thiophen-2-yl)-phenyl]-4-oxo-butyric acid, methyl ester (5.99 g, 0.0194 mol), 1.0 M aqueous sodium hydroxide (23 mL, 0.023 mol), tetrahydrofuran (50 mL), and methanol (50 mL) was stirred at room temperature for 26 hours. The resulting suspension was filtered, and the filtercake was washed with methanol. The filtercake was partitioned between dichloromethane-tetrahydrofuran-ethyl acetate (100 mL each) and 0.5 M aqueous hydrochloric acid (50 mL). The organics were washed with brine, dried ($Na_2SO_4$), and rotary evaporated to give 2.99 g of 4-[4-(5-chloro-thiophen-2-yl)-phenyl]-4-oxo-butyric acid as a bright yellow solid; mp 212–213° C.

EXAMPLE 3

4-]4-(5-Chloro-thiophen-2-yl)-phenyl]4-hydroxyimino-butyric Acid

A stirred mixture of 4-[4-(5-chloro-thiophen-2-yl)-phenyl]-4-oxo-butyric acid (0.065 g, 0.00022 mol), hydroxylamine hydrochloride (0.0181 g, 0.000260 mol), sodium carbonate (0.0280 g, 0.000260 mol), and absolute ethanol was refluxed under nitrogen for 17 hours and allowed to cool. The resulting suspension was stirred at room temperature for 2 days and filtered. The filtercake was dissolved in methanol (5 mL) and water (5 mL), and the solution was filtered to remove a small amount of fines. The filtrate was acidified with 1.0 M aqueous hydrochloric acid (0.24 mL, 0.00024 mol), and the resulting suspension was rotary evaporated to remove methanol. The resulting aqueous suspension was filtered, washed with water, and dried in vacuo to give 0.0584 g of 4-[4-(5-chloro-thiophen-2-yl)-phenyl]-4-hydroxyimino-butyric acid as a pale yellow solid; mp 172–174° C.

What is claimed is:

1. A compound of the formula

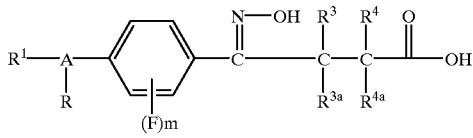

wherein m is an integer from 0 to 4;

A is

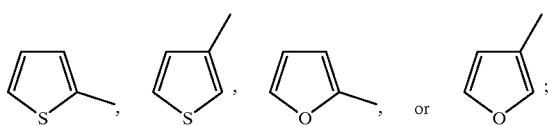

R and R¹ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
alkyl,
aryl,
arylalkyl,
heteroaryl, or
cycloalkyl,

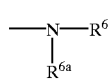

wherein $R^6$ and $R^{6a}$ are the same or different and are as defined above for $R^6$,

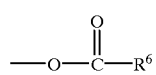

wherein $R^6$ is as defined above,

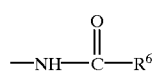

wherein $R^6$ is as defined above,

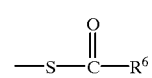

wherein $R^6$ is as defined above,

—$SR^6$ wherein $R^6$ is a defined above,

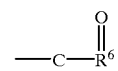

wherein $R^6$ is as defined above,
—$CH_2$—$OR^6$ wherein $R^6$ is as defined above,

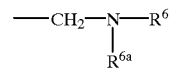

wherein $R^6$ and $R^{6a}$ are the same or different and are $R^{6a}$ as defined above for $R^6$

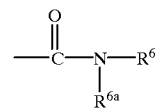

wherein $R^6$ and $R^{6a}$ are the same or different and are as defined above for $R^6$,

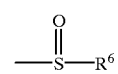

wherein $R^6$ is as defined above for,

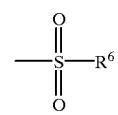

wherein $R^6$ is as defined above,
cycloalkyl, or
heteroaryl;
$R^3$, $R^{3a}$, $R^4$, and $R^{4a}$ are the same or different and are
hydrogen, or
fluorine;
and corresponding isomers thereof; or a pharmaceutically acceptable salt thereof.

2. A compound of the formula

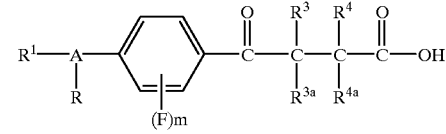

wherein m is an integer from 0 to 4;

A is

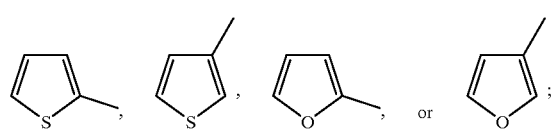

R and R¹ are the same or different and are
hydrogen,
alkyl,
halogen, nitro,
cyano,
trifluoromethyl,
$OCF_3$,
$OCF_2H$,
$OCH_2F$,
—$OR^6$ wherein $R^6$ is hydrogen,
  alkyl,
  aryl,
  arylalkyl,
  heteroaryl, or
  cycloalkyl,

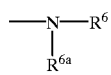

wherein $R^6$ and $R^{6a}$ are the same or different and are as defined above for $R^6$,

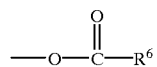

wherein $R^6$ is as defined above,

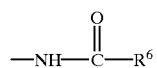

wherein $R^6$ is as defined above,

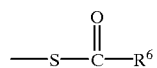

wherein $R^6$ is as defined above,
—$SR^6$ wherein $R^6$ is as defined above,

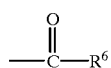

wherein $R^6$ is as defined above,
—$CH_2$—$OR^6$ wherein $R^6$ is as defined above,

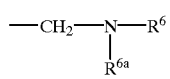

wherein $R^6$ and $R^{6a}$ are the same or different and are as defined above for $R^6$

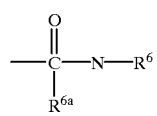

wherein $R^6$ and $R^{6a}$ are the same or different and as defined above for $R^6$,

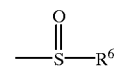

wherein $R^6$ is as defined above,

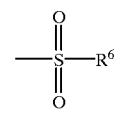

wherein $R^6$ is as defined above,
  cycloalkyl, or
  heteroaryl;
$R^3$, $R^{3a}$, $R^4$, and $R^{4a}$ are the same or different and are
  hydrogen,
  fluorine,
  alkyl,
  —$(CH_2)_n$-aryl wherein n is an integer from 1 to 6,
  —$(CH_2)_n$-heteroaryl wherein n is as defined above,
  —$(CH_2)_n$-cycloalkyl wherein n is as defined above,
  —$(CH_2)_p$—X—$(CH_2)_q$-aryl wherein X is O, S, SO, $SO_2$, or NH, and p and q are each zero or an integer of 1 to 6, and the sum of p+q is not greater than six,
  —$(CH_2)_p$—X—$(CH_2)_q$-heteroaryl wherein X, p, and q are as defined above, or
  —$(CH_2)_n$—$R^7$ wherein $R^7$ is
    N-phthalimido,
    N-2,3-napthylimido,
    —$OR^6$ wherein $R^6$ is as defined above,

wherein $R^6$ and $R^{6a}$ are the same or different and are as defined above for $R^6$,
—$SR^6$ wherein $R^6$ is as defined above,

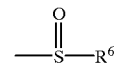

wherein $R^6$ is as defined above,

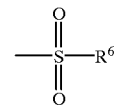

wherein $R^6$ is as defined above,

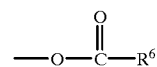

wherein R⁶ is as defined above,

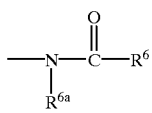

wherein R⁶ and R⁶ᵃ are the same or different and are as defined above for R⁶,

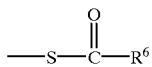

wherein R⁶ is as defined above,

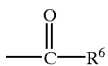

wherein R⁶ is as defined above,

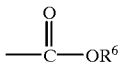

wherein R⁶ is as defined above, or

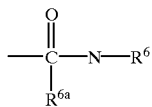

wherein R⁶ and R⁶ᵃ are the same or different and are as defined above for R⁶, and n is as defined above;

with the proviso that at least one of $R^3$, $R^{3a}$, $R^4$, or $R^{4a}$ is fluorine;

and corresponding isomers thereof; or a pharmaceutically acceptable salt thereof.

3. A compound which is 4-[4-(5-chloro-thiophen-2-yl)-phenyl]-4-oxo-butyric acid.

4. A compound selected from the group consisting of:
4-[4-(5-Chloro-thiophen-2-yl)-phenyl]-4-hydroxyimino-butyric acid;
4-[4-(5-Chloro-thiophen-2-yl)-phenyl]-4-hydroxyimino-butyric acid, 2,2-dimethyl-propionyloxymethyl ester;
4-[4-(5-Chloro-thiophen-2-yl)-phenyl]-4-methoxyimino-butyric acid;
4-[4-(5-Bromo-thiophen-2-yl)-phenyl]-4-hydroxyimino-butyric acid;
4-[4-(5-Fluoro-thiophen-2-yl)-phenyl]-4-hydroxyimino-butyric acid;
4-[4-(5-Chloro-3-fluoro-thiophen-2-yl)-phenyl]-4-hydroxyimino-butyric acid;
4-Hydroxyimino-4-[4-(5-trifluoromethyl-thiophen-2-yl)-phenyl]-butyric acid;
4-[5-(4-Chloro-phenyl)-thiophen-2-yl]-4-hydroxyimino-butyric acid;
4-[5-(4-Bromo-phenyl)-thiophen-2-yl]-4-hydroxyimino-butyric acid;
4-[5-(4-Fluoro-phenyl)-thiophen-2-yl]-4-hydroxyimino-butyric acid;
4-[5-(4-Chloro-2-fluoro-phenyl)-thiophen-2-yl]-4-hydroxyimino-butyric acid;
4-[5-(4-Cyano-phenyl)thiophen-2-yl]-4-hydroxyimino-butyric acid;
4-Hydroxyimino-4-[5-(4-trifluoromethyl-phenyl)-thiophen-2-yl)-butyric acid;
4-Hydroxyimino-4-[5-(4-methylsulfanyl-phenyl)-thiophen-2-yl)-butyric acid;
4-[4-(5-Chloro-thiazol-2-yl)-phenyl]-4-hydroxyimino-butyric acid;
4-[4-(2-Chloro-thiazol-5-yl)-phenyl]-4-hydroxyimino-butyric acid;
4-[4-(5-Chloro-1,3,4-thiadiazol-2-yl)-phenyl]-4-hydroxyimino-butyric acid;
4-[5-(4-Chloro-phenyl)-pyrimidin-2-yl]-4-hydroxyimino-butyric acid;
4-[2-(4-Chloro-phenyl)-pyrimidin-5-yl]-4-hydroxyimino-butyric acid;
4-[4-(2-Chloro-pyrimidin-5-yl)-phenyl]-4-hydroxyimino-butyric acid;
4-[4-(5-Chloro-pyrimidin-2-yl)-phenyl]-4-hydroxyimino-butyric acid;
4-[5-(4-Chloro-phenyl)-pyrazin-2-yl]-4-hydroxyimino-butyric acid;
4-[4-(5-Chloro-pyrazin-2-yl)-phenyl]-4-hydroxyimino-butyric acid;
4-[4-(5-Fluoro-isoxazol-3-yl)-phenyl]-4-hydroxyimino-butyric acid;
4-[4-(3-Fluoro-isoxazol-5-yl)-phenyl]-4-hydroxyimino-butyric acid;
4-[4-(5-Fluoro-isothiazol-3-yl)-phenyl]-4-hydroxyimino-butyric acid;
4-[4-(3-Fluoro-isothiazol-5-yl)-phenyl]-4-hydroxyimino-butyric acid;
4-Hydroxyimino-4-[4-(2-methoxy-pyrimidin-5-yl)-phenyl-butyric acid; and
4-Hydroxyimino-4-(4-pyrazol-1-phenyl)-butyric acid.

5. A compound which is 4-[4-(5-Chloro-thiophen-2-yl)-phenyl-4-hydroxyimino-butyric acid.

6. A compound according to claim 2 wherein $R^3$ and $R^{3a}$ are fluorine.

7. A compound according to claim 2 wherein $R^4$ and $R^{4a}$ are fluorine.

8. A compound according to claim 2 wherein $R^3$ is fluorine.

9. A compound according to claim 2 wherein $R^4$ is fluorine.

10. A method of inhibiting a matrix metalloproteinase comprising administering to a host suffering therefrom a therapeutically effective amount of a compound according to claim 1 in unit dosage form.

11. A method of inhibiting gelatinase A comprising administering to a host suffering therefrom a therapeutically effective amount of a compound according to claim 1 in unit dosage form.

12. A method of inhibiting stromelysin-1 comprising administering to a host suffering therefrom a therapeutically effective amount of a compound according to claim 1 in unit dosage form.

13. A method of inhibiting collagenase-3 comprising administering to a host suffering therefrom a therapeutically effective amount of a compound according to claim 1 in unit dosage form.

14. A method of preventing atherosclerotic plaque rupture comprising administering to a host suffering therefrom a therapeutically effective amount of a compound according to claim 1 in unit dosage form.

15. A method of inhibiting aortic aneurism comprising administering to a host suffering therefrom a therapeutically effective amount of a compound according to claim 1 in unit dosage form.

16. A method of preventing restenosis comprising administering to a host suffering therefrom a therapeutically effective amount of a compound according to claim 1 in unit dosage form.

17. A method of controlling periodontal disease comprising administering to a host suffering therefrom a therapeutically effective amount of a compound according to claim 1 in unit dosage form.

18. A method of treating cornmeal ulceration comprising administering to a host suffering therefrom a therapeutically effective amount of a compound according to claim 1 in unit dosage form.

19. A method of treating bums comprising administering to a host suffering therefrom a therapeutically effective amount of a compound according to claim 1 in unit dosage form.

20. A method of treating decubital ulcers comprising administering to a host suffering therefrom a therapeutically effective amount of a compound according to claim 1 in unit dosage form.

21. A method of treatment for healing wounds comprising administering to a host suffering therefrom a therapeutically effective amount of a compound according to claim 1 in unit dosage form.

22. A method of treating arthritis comprising administering to a host suffering therefrom a therapeutically effective amount of a compound according to claim 1 in unit dosage form.

23. A method of treating osteoporosis comprising administering to a host suffering therefrom a therapeutically effective amount of a compound according to claim 1 in unit dosage form.

24. A method of treating autoimmune or inflammatory disorders dependent upon tissue invasion by leukocytes comprising administering to a host suffering therefrom a therapeutically effective amount of a compound according to claim 1 in unit dosage form.

25. A method of treating multiple sclerosis comprising administering to a host suffering therefrom a therapeutically effective amount of a compound according to claim 1 in unit dosage form.

26. A method of treating inflammation and pain comprising administering to a host suffering therefrom a therapeutically effective amount of a compound according to claim 1 in unit dosage form.

27. A pharmaceutical composition comprising a compound according to claim 1 in admixture with a pharmaceutically acceptable excipient, diluent, or carrier.

28. A pharmaceutical composition comprising a therapeutically effective amount of a compound according to claim 1 in admixture with a pharmaceutically acceptable excipient, diluent, or carrier.

29. A method of inhibiting a matrix metalloproteinase comprising administering to a host suffering therefrom a therapeutically effective amount of a compound according to claim 2 in unit dosage form.

30. A method of inhibiting gelatinase A comprising administering to a host suffering therefrom a therapeutically effective amount of a compound according to claim 2 in unit dosage form.

31. A method of inhibiting stromelysin-1 comprising administering to a host suffering therefrom a therapeutically effective amount of a compound according to claim 2 in unit dosage form.

32. A method of inhibiting collagenase-3 comprising administering to a host suffering therefrom a therapeutically effective amount of a compound according to claim 2 in unit dosage form.

33. A method of preventing atherosclerotic plaque rupture comprising administering to a host suffering therefrom a therapeutically effective amount of a compound according to claim 2 in unit dosage form.

34. A method of inhibiting aortic aneurism comprising administering to a host suffering therefrom a therapeutically effective amount of a compound according to claim 2 in unit dosage form.

35. A method of preventing restenosis comprising administering to a host suffering therefrom a therapeutically effective amount of a compound according to claim 2 in unit dosage form.

36. A method of controlling periodontal disease comprising administering to a host suffering therefrom a therapeutically effective amount of a compound according to claim 2 in unit dosage form.

37. A method of treating cornmeal ulceration comprising administering to a host suffering therefrom a therapeutically effective amount of a compound according to claim 2 in unit dosage form.

38. A method of treating bums comprising administering to a host suffering therefrom a therapeutically effective amount of a compound according to claim 2 in unit dosage form.

39. A method of treating decubital ulcers comprising administering to a host suffering therefrom a therapeutically effective amount of a compound according to claim 2 in unit dosage form.

40. A method of treatment for healing wounds comprising administering to a host suffering therefrom a therapeutically effective amount of a compound according to claim 2 in unit dosage form.

41. A method of treating arthritis comprising administering to a host suffering therefrom a therapeutically effective amount of a compound according to claim 2 in unit dosage form.

42. A method of treating osteoporosis comprising administering to a host suffering therefrom a therapeutically effective amount of a compound according to claim 2 in unit dosage form.

43. A method of treating autoimmune or inflammatory disorders dependent upon tissue invasion by leukocytes comprising administering to a host suffering therefrom a therapeutically effective amount of a compound according to claim 2 in unit dosage form.

44. A method of treating multiple sclerosis comprising administering to a host suffering therefrom a therapeutically effective amount of a compound according to claim 2 in unit dosage form.

45. A method of treating inflammation and pain comprising administering to a host suffering therefrom a therapeutically effective amount of a compound according to claim 2 in unit dosage form.

46. A pharmaceutical composition comprising a compound according to claim 2 in admixture with a pharmaceutically acceptable excipient, diluent, or carrier.

47. A pharmaceutical composition comprising a therapeutically effective amount of a compound according to claim 2 in admixture with a pharmaceutically acceptable excipient, diluent, or carrier.

* * * * *

UNITED STATES PATENT AND TRADEMARK OFFICE
CERTIFICATE OF CORRECTION

PATENT NO.   : 6,399,612 B1
DATED        : June 4, 2002
INVENTOR(S)  : Purchase, Jr. et al.

It is certified that error appears in the above-identified patent and that said Letters Patent is hereby corrected as shown below:

<u>Title page,</u>
Item [56], References Cited, OTHER PUBLICATIONS, the following references should be inserted into the list of OTHER PUBLICATIONS after "R.G. Child," Fenbufen . . . :

-- R.K. Clark et al., "Development of Tissue Damage, Inflammation and Resolution Following Stroke: An Immunohistochemical and Quantitative Planimetric Study", Brain Research Bulletin, Vol. 31, pp. 565-572, 1993

N.R. Cooper et al., "Key Issues in Alzheimer's Disease Inflammation," Neurobiology of Aging 21 (2000)) 451-453

B. Davies et al., "A Synthetic Matrix Metalloproteinase Inhibitor Decreases Tumor Burden and Prolongs Survival of Mice Bearing Human Ovarian Carcinoma Xenografts," Cancer Research 53, 2087-2091, May 1, 1993

Y.A. DeClerck et al., "Inhibition of Invasion and Metastatis in Cells Transfected with an Inhibitor of Metalloproteinases," Cancer Research 52, 701-708, February 1, 1992

A.J. Ellis et al., "The Prevention of Collagen Breakdown in Bovine Nasal Cartilage by TIMP, TIMP-2 and a Low Molecular Weight Synthetic Inhibitor," Biochemical and Biophysical Research Communications, Vol. 201, No. 1, May 30, 1994, pp. 94-101

J.M.P. Freije et al., "Molecular Cloning and Expression of Collagenase-3, a Novel Human Matrix Metalloproteinase Produced by Breast Carcinomas," The Journal of Biological Chemistry, Vol. 269, No. 24, June 17, 1994, pp. 16766-16773

Z.S. Galis et al., "Increased Expression of Matrix Metalloproteinases and Matrix Degrading Activity in Vulnerable Regions of Human Atherosclerotic Plaques," J. Clin. Invest., Vol. 94, December 1994, 2493-2503

H.E. Gendelman et al., "Macrophages/Microglia and the Pathophysiology of CNS Injuries in AIDS," Journal of Leukocyte Biology, Vol. 56, September 1994, pp. 387-388

UNITED STATES PATENT AND TRADEMARK OFFICE
CERTIFICATE OF CORRECTION

PATENT NO.    : 6,399,612 B1
DATED         : June 4, 2002
INVENTOR(S)   : Purchase, Jr. et al.

It is certified that error appears in the above-identified patent and that said Letters Patent is hereby corrected as shown below:

K. Gijbels et al., "Reversal of Experimental Autoimmune Encephalomyelitis with a Hydroxamate Inhibitor of Matrix Metalloproteases," J. Clin Invest., Vol. 94, December 1994, 2177-2182

D. Giulian et al., "Inflammatory Glia Mediate Delayed Neuronal Damage After Ischemia in the Central Nervous System," Stroke. 1993; 24 [Suppl. I]:I-84-I-90

A.M. Henney et al., "Localization of Stromelysin Gene Expression in Atherosclerotic Plaques by *in situ* Hybridization," Proc. Natl. Acad. Sci. USA, Vol. 88, pp. 8154-8158, September 1991

T.H. Lee et al., "Impact of Left Ventricular Cavity Size on Survival in Advanced Heart Failure," The American Journal of Cardiology, Vol. 72, September 15, 1993, pp. 672-676

P.N. Leigh, "Pathogenic Mechanisms in Amyotrophic Lateral Sclerosis and Other Motor Neuron Disorders," In: Calne D.B., ed. Neurodegenerative Diseases, W. B. Saunders, 1994:473-88

OTHER PUBLICATIONS, page 2, please delete duplicate references beginning with "The Canadian Study of Health and Aging . . . and all references on page 3.

Column 53,
Line 11, the carboxyl "C" should be added to the diagram.

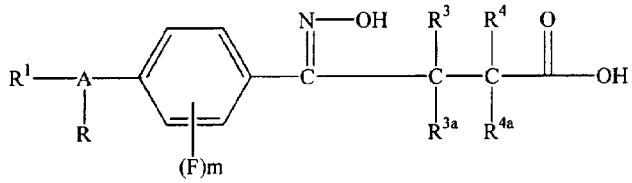

should be

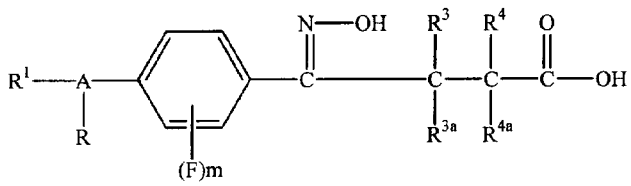

UNITED STATES PATENT AND TRADEMARK OFFICE
CERTIFICATE OF CORRECTION

PATENT NO. : 6,399,612 B1
DATED : June 4, 2002
INVENTOR(S) : Purchase, Jr. et al.

It is certified that error appears in the above-identified patent and that said Letters Patent is hereby corrected as shown below:

Column 54,
Line 30, delete the word "for" after "above".

Column 55,
Lines 60-64, "$R^{6a}$" should be under "N"

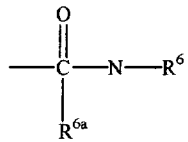

should be

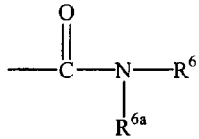

Column 57,
Lines 30-34, "$R^{6a}$" should be under "N"

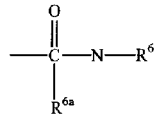

should be

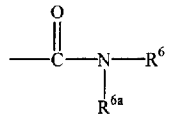

UNITED STATES PATENT AND TRADEMARK OFFICE
CERTIFICATE OF CORRECTION

PATENT NO. : 6,399,612 B1
DATED : June 4, 2002
INVENTOR(S) : Purchase, Jr. et al.

It is certified that error appears in the above-identified patent and that said Letters Patent is hereby corrected as shown below:

Column 59,
Line 18, "bums" should read -- burns --

Column 60,
Line 26, "bums" should read -- burns --

Signed and Sealed this

Eighteenth Day of February, 2003

JAMES E. ROGAN
*Director of the United States Patent and Trademark Office*